(12) United States Patent
Grissom et al.

(10) Patent No.: US 6,797,521 B2
(45) Date of Patent: Sep. 28, 2004

(54) FLUORESCENT COBALAMINS AND USES THEREOF

(75) Inventors: Charles B. Grissom, Salt Lake City, UT (US); Frederick G. West, Salt Lake City, UT (US); James McGreevy, Salt Lake City, UT (US); Joel S. Bentz, Salt Lake City, UT (US); Michelle J. Cannon, Price, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 10/097,646

(22) Filed: Mar. 15, 2002

(65) Prior Publication Data

US 2002/0192683 A1 Dec. 19, 2002

Related U.S. Application Data

(63) Continuation-in-part of application No. PCT/US00/29370, filed on Oct. 26, 2000.
(60) Provisional application No. 60/161,368, filed on Oct. 26, 1999, and provisional application No. 60/276,036, filed on Mar. 16, 2001.

(51) Int. Cl.$^7$ ..................... G01N 33/567; A61K 31/70; C07H 23/00
(52) U.S. Cl. .................... 436/505; 514/52; 536/26.44; 435/4; 435/7.1; 435/7.21; 435/7.23; 436/63; 436/64; 436/164; 436/172
(58) Field of Search .................. 536/26.44; 514/52; 436/505

(56) References Cited

U.S. PATENT DOCUMENTS

| | | | | |
|---|---|---|---|---|
| 4,337,246 A | * | 6/1982 | Iwagiri et al. ................ 514/52 |
| 4,465,775 A | * | 8/1984 | Houts ........................ 436/503 |
| 4,994,373 A | * | 2/1991 | Stavrianopoulos et al. .... 435/6 |
| 5,294,536 A | * | 3/1994 | Palumbo .................... 435/7.93 |
| 5,548,064 A | * | 8/1996 | Russell-Jones et al. ..... 530/380 |
| 5,739,287 A | * | 4/1998 | Wilbur et al. ............... 530/367 |
| 5,739,313 A | | 4/1998 | Collins et al. |
| 5,840,712 A | * | 11/1998 | Morgan, Jr. et al. .......... 514/52 |
| 5,840,880 A | * | 11/1998 | Morgan, Jr. et al. ....... 536/26.4 |
| 6,004,533 A | | 12/1999 | Collins et al. |
| 6,083,926 A | * | 7/2000 | Morgan, Jr. et al. .......... 514/52 |
| 6,096,290 A | | 8/2000 | Collins et al. |
| 6,211,355 B1 | | 4/2001 | Collins et al. |

FOREIGN PATENT DOCUMENTS

WO  WO 94/27613 A1 * 12/1994
WO  WO 98/08859 A1 * 3/1998

OTHER PUBLICATIONS

Mitchell et al., "Targeting Leukemia Cells with Cobalamin Bioconjugates," in *Enzymatic Mechanisms*, Frey & Northrup (eds.), IOS Press, 1999, Assession No.: 343381, only pp. 150–154 supplied.*
Hogenkamp et al., "Diagnostic and Therapeutic Analogues of Cobalamin," Chapter 15 in *Chemistry and Biochemistry of $B_{12}$*, R. Banerjee (ed.), John Wiley & Sons, 1999, New York, NY, only pp. 385–410 supplied.*
Rosendahl et al., "Synthesis and Biological Activity of a Profluorescent Analog of Coenzyme $B_{12}$," *Proc. Natinal Academy of Sciences USA*, 79(11), 3480–3484 (Jun., 1982).*
Jacobsen, "Preparation of Cryptofluorescent Analogs of Cobalamin Coenzymes," *Methods in Enzymology*, 67(Vitamins and Coenzymes, Pt. F), 12–19 (1980).*
Jacobsen et al., "Cryptofluorescent Analogs of Cobalamin Coenzymes: Synthesis and Characterization," *Journal of Inorganic Biochemistry*, 10(1), 53–65 (1979); *Chemical Abstracts*, 83(13), p. 599, Abstract No. 114791c (Sep. 29, 1975); also Abstract and equivalent HCAPlus document supplied.*
Moskophidis et al., "Partial Synthesis of Adenosylcorrinoids and of 1,$N^6$–Ethenoadenosylcobalamin with a Fluorescent Nucleoside," *Zeitschrift für Naturforschung, C: Biosci.*, 30c(7–8), 460–465 (1975); *Chemical Abstracts*, 91(7), p. 262, Abstract No. 5175q (Aug. 13, 1979);.*

* cited by examiner

Primary Examiner—James O. Wilson
Assistant Examiner—Lawrence Crane
(74) Attorney, Agent, or Firm—Rothwell Figg Ernst & Manbeck

(57) ABSTRACT

The present invention relates to fluorescent cobalamins and uses of these compounds. More particularly, this invention relates to fluorescent cobalamins that comprise a fluorescent, phosphorescent, luminescent or light-producing compound covalently linked to cobalamin. These fluorescent cobalamins can be used to as diagnostic and prognostic markers (a) to distinguish cancer cells and tissues from healthy cells and tissues, including identifying lymph nodes containing cancer cells, and (b) to determine if an individual will respond positively to chemotherapy using cobalamin-therapeutic bioconjugates.

28 Claims, 17 Drawing Sheets

| R | TCII | Non-IF | IF |
|---|---|---|---|
| OH | 110 +/- 10 pM | 137 +/- 23 pM | 100 +/- 10 pM |
| CN | 130 +/- 30 pM | 137 +/- 49 pM | 130 +/- 37 pM |
| CH3 | 140 +/- 22 pM | 152 +/- 35 pM | 101 +/- 41 pM |
| | 190 +/- 82 pM | 113 +/- 10 pM | 100 +/- 40 pM |

FIG. 12A

| R | TCII | Non-IF | IF |
|---|---|---|---|
| CNCbl-b-COOH | 410 +/- 18 pM | 110 +/- 37 pM | 100 +/- 10 pM |
| CNCbl-b-(5-aminopentylamide) | 430 +/- 100 pM | 159 +/- 27 pM | 100 +/- 17 pM |
| CNCbl-c-COOH | 230 +/- 24 pM | 261 +/- 150 pM | 483 +/- 130 pM |
| CNCbl-d-COOH | 280 +/- 10 pM | 100 +/- 17 pM | 100 +/- 32 pM |
| CNCbl-e-COOH | 280 +/- 20 pM | 135 +/- 41 pM | 100 +/- 22 pM |

FIG. 12B

FLUORESCENT COBALAMINS AND USES THEREOF

CROSS-REFERENCE TO RELATED APPLICATIONS

The present application is a continuation-in-part of International application No. PCT/US00/29370, filed Oct. 26, 2000 designating the United States, and also claims priority under 19 USC §119(e) to U.S. provisional patent application Serial Nos. 60/161,368, filed Oct. 26, 1999 and 60/276,036, filed Mar. 16, 2001, each application incorporated herein by reference.

This invention was made in part with Government support under Grant Nos. R01 CA73003 and CA87685 awarded by the National Institutes of Health, Bethesda, Md. The United States Government has certain rights in the invention.

BACKGROUND OF THE INVENTION

The present invention relates to fluorescent cobalamins (sometimes referred to herein as CobalaFluors) and uses of these compounds. More particularly, this invention relates to fluorescent cobalamins comprised of a fluorescent, phosphorescent, luminescent or light-producing compound that is covalently linked to cobalamin. These fluorescent cobalamins can be used as diagnostic and prognostic markers (a) to distinguish cancer cells and tissues from healthy cells and tissues, including identifying lymph nodes containing cancer cells, and (b) to determine if an individual will respond positively to chemotherapy using cobalamin-based therapeutic bioconjugates.

The publications and other materials used herein to illuminate the background of the invention, and in particular cases, to provide additional details respecting the practice, are incorporated by reference, and for convenience are referenced in the following text by author and date and are listed alphabetically by author in the appended bibliography.

Rapidly-dividing cells require cobalamin as a cofactor for the enzyme methionine synthase to support one-carbon metabolism prior to DNA replication (Hogenkamp et al., 1999). In acute promyelocytic leukemia, a 3–26 fold increase in the unsaturated $B_{12}$ binding capacity of blood is observed, due to an increase in the concentration of the $B_{12}$ binding proteins transcobalamin and haptocorrin (Schneider, et al., 1987; Rachimelwitz, et al., 1971). Some patients with solid tumors also exhibit a significant increase in the circulating levels of transcobalamin and haptocorrin (Carmel, et al., 1975). The increase in unsaturated serum cobalamin binding capacity corresponds to the increased uptake of cobalamin by rapidly dividing cells. Tumors even sequester sufficient cobalamin for diagnostic imaging purposes if a gamma-emitting radionuclide, such as $^{111}In$, is attached to cobalamin through the octadentate chelator diethylenetriaminepentaacetic acid (DTPA) (Hogenkamp and Collins, 1997). This has been demonstrated in mice with an implanted fibrosarcoma (Hogenkamp and Collins, 1997), as well as in humans with breast cancer (Collins et al., 1999), and in tumors of the prostate, lung, and brain (Collins et al., 2000).

In the sentinel lymph node concept for melanoma and breast cancer surgery, a dye or radionuclide is injected into the tissue around the tumor to identify the first lymph node that drains the tumor (Morton et al., 1992; McGreevy, 1998). This node is termed the sentinel node, and it is removed for diagnostic tests to determine the extent of metastasis beyond the primary tumor. This procedure is controversial, as it fails to detect metastatic disease in about 12% of patients (McMasters et al., 1999). The dye or radionuclide that is injected is not specific for cancer cells, but merely identifies for the surgeon the primary lymph node that drains the region of the tumor. The high false-negative rate should be improved dramatically by using a fluorescent marker that is specific for cancer cells.

Thus, there exists a need for an agent that can be used for the diagnosis and prognosis of cancer tissue or cells with improved results.

SUMMARY OF THE INVENTION

The present invention relates to fluorescent cobalamins and uses of these compounds. More particularly, this invention relates to fluorescent cobalamins comprised of a fluorescent, phosphorescent, luminescent or light-producing compound that is covalently linked to cobalamin. These fluorescent cobalamins can be used as a diagnostic and prognostic marker (a) to distinguish cancer cells and tissues from healthy cells and tissues, including identifying lymph nodes containing cancer cells, and (b) to determine if an individual will respond positively to chemotherapy using cobalamin-therapeutic bioconjugates. The fluorescent cobalamins of the present invention offer the necessary properties of (1) rapid transport and storage by cancer cells (maximum uptake occurs at 4–6 hours), (2) a bright fluorophore that can be visually detected at very low concentrations, and (3) nontoxic components.

In one aspect of the present invention, fluorescent cobalamins are provided in which fluorescent, phosphorescent, luminescent or light-producing compounds are covalently linked to cobalamin (vitamin $B_{12}$). The fluorescent, phosphorescent or light-producing compounds can be covalently linked to the cobalt atom, the corrin ring, or the ribose moiety of cobalamin. It is preferred to covalently link the fluorescent, phosphorescent, luminescent or light-producing compound to the corrin ring or the ribose moiety. Although, any fluorescent, phosphorescent, luminescent or light-producing compound can be utilized in preparing the fluorescent cobalamins, it is preferred to utilize fluorescent, phosphorescent, luminescent or light-producing compounds that are excitable with visible or infrared light. Examples of preferred fluorescent compounds include, but are not limited to, fluorescein, fluorescein-5EX, methoxycoumarin, naphthofluorescein, BODIPY 493/503, BODIPY FL, BODIPY R6G, BODIPY 530/550, BODIPY TMR, BODIPY 564/570, BODIPY 576/589, BODIPY 581/591, BODIPY TR, Cascade Blue, Dansyl, Dialkylaminocoumarin, 4',5'-dichloro-2',7'-dimethyoxyfluorescein, 2',7'-dichlorofluorescein, eosin, eosin F3S, erythrosin, hydroxycoumarin, lissamine rhodamine B, methosycoumarin, maphthofluorescein, NBD, Oregon Green 488, Oregon Green 500, Oregon Green 514, PyMPO, pyrene, rhodamine 6G, rhodamine green, rhodamin red, rhodol green, 2',4',5',7'-tetrabromosulfonefluorescein, tetramethylrhodamine (TMR), Texas Red, X-rhodamine, Cy2 dye, Cy3 dye, Cy5 dye, Cy5.5 dye, or a quantum dot stricture. The preferred fluorescent cobalamins of the present invention fluoresce when excited by visible or infrared light without the need to separate the fluorescent or phosphorescent compound from cobalamin. The light may be provided by a laser or a fiber optic light source with appropriate filter. Red light is preferred for better tissue penetration.

In a second aspect of the present invention, the fluorescent cobalamins are used to distinguish cancer cells from healthy cells. In one embodiment of this aspect of the invention, a fluorescent cobalamin is administered to a patient prior to surgery. The presence of fluorescence, phosphorescence, luminescence or emited light in cancer cells is used by the surgeon to define the tissue to be removed, whether in a primary tumor or in a metastatic site. In a second embodiment, a fluorescent cobalamin is administered to a patient in a maimer suitable for uptake by lymph nodes draining the situs of the tumor. The presence of fluorescence, phosphorescence, luminescence or emited light identifies those lymph nodes that should be removed during surgery. In this latter embodiment, laparoscopic, endoscopic and microscopic techniques can be utilized to identify lymph nodes with cancer cells. The use of these techniques facilitates the identification and retrieval of positive lymph nodes.

In a third aspect of the present invention, the fluorescent cobalamins are used to determine if an individual will respond positively to chemotherapy using cobalamin-based therapeutic bioconjugates. In this aspect, a fluorescent cobalamin is used to assess the ability of the particular cancer cell type to transport and store cobalamin, both qualitatively and quantitatively. Various types of cancer that transport and store large amounts of cobalamin are good candidates for therapy with cobalamin-based therapeutic bioconjugates. Quantification of tumor cell cobalamin binding, uptake, transport, and storage can be carried out by measuring the fluorescence under visual inspection (e.g. tissue slide), by epifluorescence microscopy, fluorescence laparoscopy, fluorescence endoscopy or flow cytometry.

In a fourth aspect of the present invention, the fluorescent cobalamins are used to determine the levels of cobalamin in blood, plasma, serum, cerebrospinal fluid or urine or to determine the amount of unbound cobalamin binding capacity in blood, plasma, serum or cerebrospinal fluid.

In a fifth aspect of the present invention, any fluorescent molecule (cancer-targeted or non-targeted) can be detected in a lymph node using to laparoscopic or endoscopic visualization.

BRIEF DESCRIPTION OF THE DRAWINGS

FIGS. 12A–12C show the Kd values for cobalamin, cobalamin analogs and CobalaFluors.

DETAILED DESCRIPTION OF THE INVENTION

The present invention relates to fluorescent cobalamins and uses of these compounds. More particularly, this invention relates to fluorescent cobalamins that comprise a fluorescent compound (fluorophore), a phosphorescent compound (phosphorophore), a luminescent compound (chemiluminescent chromophore) or a light-producing compound that is covalently linked to cobalamin (vitamin $B_{12}$). These fluorescent cobalamins can be used as diagnostic and prognostic markers (a) to distinguish cancer cells and cancerous tissue from healthy cells and tissues, including identifying lymph nodes containing cancer cells, and (b) to determine if an individual will respond positively to chemotherapy using cobalamin-therapeutic bioconjugates.

The fluorescent cobalamins of the present invention can be represented by the following formula

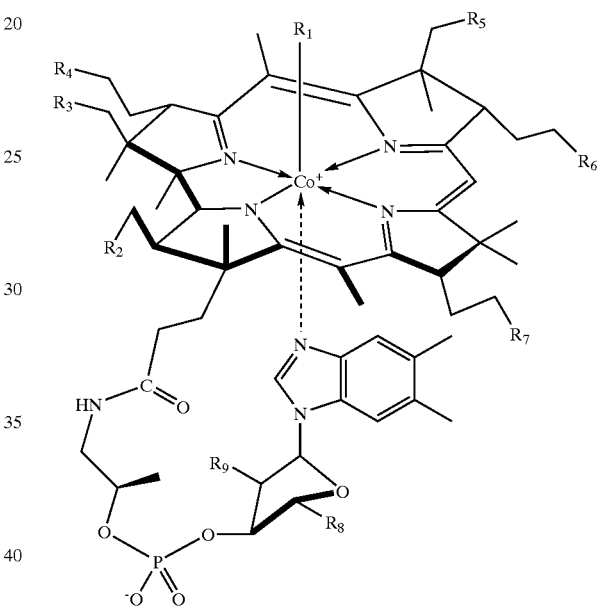

where $R_1$ is CN, OH, $OH_2$, $CH_3$, 5'-deoxyadenosine or $(CH_2)_p NHC(=S)Y$; $R_2$, $R_3$, $R_4$, $R_5$, $R_6$, and $R_7$ are independently $CONH_2$ or $CO—X_mY$; $R_8$ is $CH_2OH$ or $CH_2O(C=O)$ $X_mY$; $R_9$ is OH or $O(C=O)X_mY$; X is a linker having the formula $N(CH_2)_n NHO(C=O)$ or $NH—(CH_2)_n—NH$; Y is a fluorophore, a phosphorophore, chemiluminescent chromophore or a light-producing molecule; m is 0 or 1, n is 0–50 and p is 2–10, with the proviso that at least one of $R_1$–$R_9$ groups contains Y. It is preferred that at least $R_8$ contains Y.

The fluorescent cobalamins of the present invention are prepared by covalently attaching a fluorophore, a phosphorophore, chemiluminescent chromophore or a light-producing molecule to cobalamin. The fluorophore, phosphorophore, chemiluminescent chromophore or light-producing molecule is covalently linked to the cobalt atom, to the corrin ring or to the ribose sugar directly or via a linker molecule. The covalent linkage is preferably accomplished with the use of a linker molecule. If the fluorophore, phosphorophore, chemiluminescent chromophore or light-producing molecule is attached to the cobalt atom of cobalamin, the fluorescence, phosphorescence or emitted light is diminished in intensity through quenching by the spin of the cobalt atom. In addition, prolonged exposure of the fluorescent cobalamin to light will cleave the cobalt-carbon bond and release the fluorophore, phosphorophore, chemiluminescent chromophore or light-producing molecule from cobalamin (Howard et al., 1997). Thus, it is preferred to attach the fluorophore, phosphorophore, chemiluminescent chromophore or light-producing molecule to the corrin ring or the ribose moiety of the cobalamin molecule. These latter fluorescent cobalamins do not have the disadvantages of the fluorescent cobalamins in which the fluorophore, phosphorophore, chemiluminescent chromophore or light-producing molecule is covalently linked to the cobalt atom.

Figure 1:
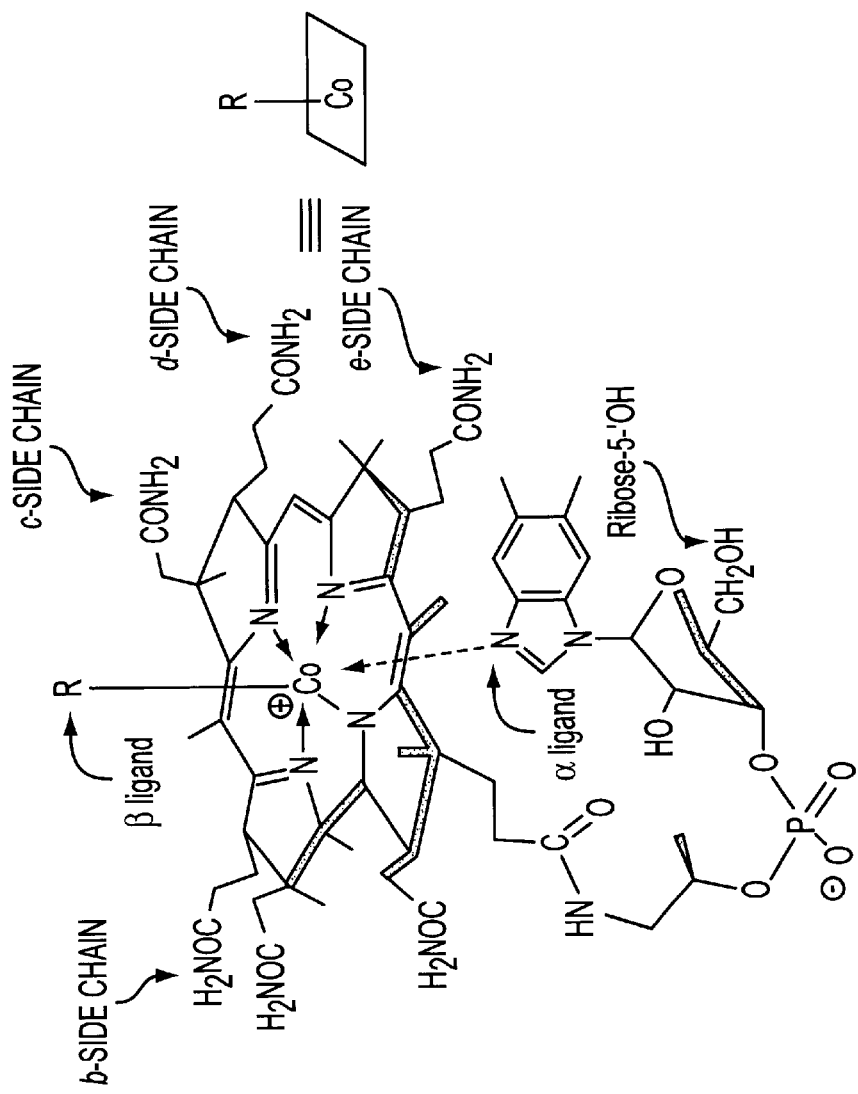
FIG. 1 shows sites for modification on the cobalamin molecule.

Attachment of the fluorophore, phosphorophore, chemiluminescent chromophore or light-producing molecule to a carboxylate on the corrin ring or the 5'-ribose hydroxyl group circumvents the problem of lower sensitivity and photolability. In general, corrin ring carboxylate derivatives (Collins and Hogenkamp, 1997) are known, but none of the compounds synthesized have contained a fluorescent marker. The fluorophore, phosphorophore, chemiluminescent chromophore or light-producing molecule can be attached directly to the corrin ring, rather than to the cobalt atom by derivatization of the cobalamin monocarboxylate according to published methods (Collins and Hogenkamp, 1997 and references cited therein). FIG. 1 shows sites on cobalamin which can be used for modification in accordance with the present invention.

Although, any fluorophore, phosphorophore, chemiluminescent chromophore or light-producing molecule can be utilized in preparing the fluorescent cobalamins, it is preferred to utilize fluorophores that are excitable with visible or infrared light. It is preferred to use visible or infrared light for in vivo use of the fluorescent cobalamins. Examples of preferred fluorophores include, but are not limited to, fluorescein, fluorescein-5EX, methoxycoumarin, naphthofluorescein, BODIPY 493/503, BODIPY FL, BODIPY R6G, BODIPY 530/550, BODIPY TMR, BODIPY 564/570, BODIPY 576/589, BODIPY 581/591, BODIPY TR, Cascade Blue, Dansyl, Dialkylaminocoumarin, 4',5'-dichloro-2',7'-dimethyoxyfluorescein, 2',7'-dichlorofluorescein, eosin, eosin F3S, erythrosin, hydroxycoumarin, lissamine rhodamine B, methosycoumarin, maphthofluorescein, NBD, Oregon Green 488, Oregon Green 500, Oregon Green 514, PyMPO, pyrene, rhodamine 6G, rhodamine green, rhodamin red, rhodol green, 2',4',5',7'-tetrbromosulfonefluorescein, tetramethylrhodamine (TMR), Texas Red, X-rhodamine, Cy2 dye, Cy3 dye, Cy5 dye, Cy5.5 dye, or a quantum dot structure. The preferred fluorescent cobalamins of the present invention fluoresce when excited by visible or infrared light without the need to cleave the fluorophore from the bioconjugate. The light may be provided by a laser or a fiber optic light source with an appropriate filter. Red light is preferred for better tissue penetration.

It has been found that there is differential uptake of fluorescent cobalamin analogues in normal and leukemic human bone marrow. The difference between normal marrow cells and leukemic myeloblasts (cancer cells) is particularly noteworthy, with no detectable cobalamin being taken up by normal cells. Bone marrow samples from healthy individuals show no fluorescent labeling. It has also been found that there is uptake of a doxorubicin-cobalamin conjugate, originally synthesized as a potential chemotherapeutic compound. Cellular uptake of the doxorubicin-cobalamin conjugate can be observed in P-388 murine leukemia cells, as well as in HCT-116 human colon tumor cells. Thus, the uptake of fluorescent derivatives of cobalamin occurs in leukemia and solid tumor cell lines. These results, in combination with the knowledge that all cancer cells increase cobalamin transport and storage, demonstrate the general applicability of the use of fluorescent cobalamins to distinguish cancer cells from normal cells.

Thus, the fluorescent cobalamins of the present invention can be used to:
 identify cancerous tissue visually, via fluorescence microscopy, fluorescence laparoscopy, fluorescence endoscopy, or flow cytometry,;
 identify cancerous cells in tissue sections or samples from tissue biopsies;
 define tumor margins in vivo, ex vivo or in situ;
 diagnose, detect, prognose, predict or monitor cancer in vivo, ex vivo or in situ;
 identify metastatic cancer in vivo, ex vivo or in situ;
 determine the stage of cancer progression;
 identify cancer transdermally;
 identify metastatic cancer transdermally;
 identify cancer in lymph nodes, including in the sentinel lymph node or nodes or in an axillary lymph node or nodes, including with the use of minimally invasive techniques, such as laparoscopy or endoscopy;
 identify metastatic disease in the treatment, detection, prediction, prognostication or monitoring of cancer, such as breast cancer, ovarian cancer, lung cancer, prostate cancer, epithelial cancer (adenocarcinoma), liver cancer, melanoma and lymphoma;
 conduct flow cytometry studies of bone marrow aspirates or peripheral blood samples for diagnosing, predicting, prognosticating, monitoring or characterizing leukemia or lymphoma;
 predict whether a patient will respond positively to chemotherapy that is based on the use of a cobalamin-therapeutic bioconjugate;
 improve the definition of tumor micromargins in a biopsy or lumpectomy;
 decrease the chance of leaving cancerous cells behind in a biopsy, lumpectomy, or tumorectomy and thereby reduce the need for follow-up surgery to remove the remaining cancer cells.

Prediction refers to understanding the biological behavior of the tumor, and how the tumor will respond (favorably or unfavorably) to therapy. Prognosis refers to the anticipated patient outcome following therapy (i.e. what is the likelihood of five- or ten-year survival following therapy). Monitoring refers to determining the success of therapy and detection of residual disease following treatment. An example is the use of a fluorescent cobalamin conjugate to test the bone marrow for the presence of myeloblasts following treatment of leukemia. Characterization refers to a descriptive or quantitative classification of the type of tumor in comparison to closely related types of tumors.

The fluorescent cobalamins of the present invention can be administered in accordance with customary cancer diagnostic, detection, prediction, prognostication, monitoring or characterization methods known in the art. For example, the fluorescent cobalamins can be administered intravenously, intrathecally, intratumorally, intramuscularly, intralymphatically, or orally. Typically, an amount of the fluorescent cobalamin of the present invention will be admixed with a pharmaceutically acceptable carrier. The carrier may take a wide variety of forms depending on the form of preparation desired for administration, e.g., oral, parenteral, intravenous, intrathecal, intratumoral, circumtumoral, and epidural. The compositions may further contain antioxidizing agents, stabilizing agents, preservatives and the like. Examples of techniques and protocols can be found in *Remington's Pharmaceutical Sciences*. The amount of fluorescent cobalamin to be administered will typically be 1–500 mg.

As shown herein, cobalamin analogs are recognized by cobalamin transport proteins, such as haptocorrin (TCI or HC), intrinsic factor (IF) or transcobalamin (TCII), with high affinity. The attachment of large molecules to cobalamin does not appear to affect protein binding.

An improvement in the surgeon's ability to identify metastatic disease in lymph nodes will advance surgical therapy by preserving, e.g., healthy tissue and minimizing the number of axillary lymph nodes removed. This will improve the patient's quality of life and improve morbidity and long-term mortality. Precise identification of cancer cells that have spread to lymph nodes will allow removal of only the diseased ducts and nodes, while sparing the healthy axillary nodes. This invention is extremely valuable. For example, with 186,000 new cases of breast cancer each year, the number of surgeries to remove primary tumors and determine the status of associated lymph nodes is significant. The perfunctory removal of all axillary lymph nodes and ducts leads to local edema and increased morbidity. The non-removal of axillary lymph nodes and ducts that contain metastatic cancer cells leads to decreased survival and increased long-term mortality.

In the sentinel lymph node biopsy approach, a blue dye and/or radioactive tracer are injected into the breast near the tumor. A small incision is made under the arm to look for traces of the dye or radioactivity to identify the lymph node(s) that drain the area of the breast and, as a consequence, are most likely to contain metastatic cancer cells. In accordance with the present invention, a fluorescent cobalamin replaces the blue dye and radioisotope tracer currently used in sentinel lymph node biopsies. The use of the fluorescent cobalamins of the present invention enables the application of the sentinel lymph node biopsy approach to all types of cancer. In addition, the fluorescent cobalamins of the present invention enables the use of minimally invasive techniques, such as laparoscopic, endoscopic and microscopic techniques, in the analysis of cancer, especially the analysis of cancer cells in lymph nodes. The use of the fluorescent cobalamins will facilitate the identification and retrieval of positive lymph nodes. Thus, in accordance with the present invention, the fluorescent cobalamins can be used with the following cancers or cancers of: breast, skin (melanoma), gynecological (ovarian, prostate, uterine, cervical, vulval, penal, testicular), head and neck (lip, tongue, mouth, pharynx), digestive organs (esophageal, stomach, small intestine, large intestine, rectum, colon, liver, pancreas), bone, connective tissue, urinary organs (bladder, kidney), eye, brain and central nervous system, endocrine glands (thyroid), lymph tissues, hodgkin's disease, non-hodgkins lymphoma and multiple myeloma.

In addition, the use of fluorescent cobalamins of the present invention enables the use of minimally invasive techniques, such as laparoscopic and endoscopic techniques, to the identification of lymph nodes which contain cancer cells and which must be removed. This proposed technology is designed to replace the two current methods of surgically examining the axillary lymph nodes in patients with operable breast cancer with a more accurate and less painful method. The two operations now in use are the standard axillary node dissection using a large incision (approximately 5 inches) and removing all of the lower level lymph nodes (10–15). The second, and currently experimental method, is the sentinel lymph node biopsy. This method uses either a visual dye or a gamma emitter to identify the first lymph node to drain the breast. This requires a similarly large incision and a technically challenging examination of the lymphatic pathways. The cobalamin molecules of the present invention will take a photophore to the nodes with cancer. The lymph nodes are examined directly through three small incisions (3–5 mm) using laparoscopic instruments. The closed operative technique provides a dark field for laser excitation. The bright emission of stimulated light from the cobalamin-photophore conjugate in the tumor bearing lymph nodes will facilitate identification and retrieval of positive lymph nodes. This method will result in less dissection, less pain and better accuracy. Similar principles apply to using the fluorescent cobalamins to detect cancer cells with endoscopic techniques.

Furthermore, since the fluorescent cobalamins of the present invention are differentially taken up by cancer cells, these fluorescent cobalamins are an improved marker that will allow surgeons to excise cancerous tissue selectively, thereby leaving healthy tissue.

The ability of fluorescent cobalamins bound to cancer cells to be detected laparoscopically or endoscopically demonstrates that fluorescent molecules can be used to determine a sentinel lymph node laparoscopically or endoscopically. Thus, any fluorescent molecule (cancer-targeted or non-targeted) can be detected in a lymph node using to laparoscopic or endoscopic visualization. As an example, a red fluorophore could be injected intratumorally as is now done in the sentinel lymph node procedure. Insufflation of the axilla would allow the surgeon to find the fluorescent node laparoscopically (through 2 small incisions) and thereby avoid the use of a radioactive tracer to help the surgeon find the general location of the sentinel node.

The fluorescent cobalamins of the present invention offer several improvements as an intraoperative marker. These improvements include:

The fluorescent marker will be specific for cancer cells in lymph ducts and nodes, rather than simply indicating which node is draining the tidal basin. The fluorescent marker will also distinguish cancer cells from healthy cells.

The marker can be used in low concentrations because of the inherent sensitivity afforded by fluorescence detection. The blue dye now in use tends to obscure the active node and complicates postsurgical examination of the tissue by a pathologist. The blue dye also tends to obscure bleeding vessels, thereby complicating surgical excision of the node and subsequent wound closure. The use of a fluorescent marker should avoid these problems.

A fluorescent marker that is specific for cancer cells will improve the false-negative rate of 5–10%, as is seen with the procedure as currently practiced.

A decreased false-negative rate would improve the acceptance of this technique by patients and surgeons. This might decrease the training time necessary (typically 30 or more cases with complete axial node dissection) for a surgeon to learn this procedure.

The fluorescent marker enables the use of laparoscopic, endoscopic and microscopic techniques for the visualization of cancer cells. These techniques can also be used to visualize primary tumors, metastatic tumors, axillary lymph nodes, inguinal lymph nodes and cervical lymph nodes. These techniques will reduce the necessity for large incisions and technically challenging examination of lymphatic pathways in the analysis of cancer. These techniques will result in less dissection, less pain and better accuracy.

In a further embodiment of the present invention, the fluorescent cobalamins can be used in a competitive binding assay to determine the concentration or amount of naturally-occurring cobalamin (hydroxocobalamin, methylcobalamin, adenosylcobalamin, or cyanocobalamin) in blood, plasma, serum, or other bodily fluids. In this type of assay, a fluorescent cobalamin is used in place of radioactively-labelled cobalamin in a competitive binding assay, well known to a skilled artisan. Radioactive assays for cobalamin have been described in U.S. Pat. Nos. 6,096,290; 5,614,394; 5,227,311; 5,187,107; 5,104,815; 4,680,273; 4,465,775; 4,355,018, among others, each incorporated herein by reference. This assay procedure can be used to determine the amount of unsaturated cobalamin binding capacity in blood, plasma, serum, or bodily fluids, as well as the concentration of cobalamin that is bound to the proteins transcobalamin, haptocorrin, or intrinsic factor. The use of fluorescent cobalamins has a significant advantage over radioactively-labelled cobalamin in a clinical chemistry binding assay because it does not require the special shipping, handling, and disposal procedures associated with radioactively-labelled cobalamin.

EXAMPLES

The present invention is further described by reference to the following Examples, which are offered by way of illustration and are not intended to limit the invention in any manner. Standard techniques well known in the art or the techniques specifically described below were utilized.

Example 1

Synthesis of Fluorescent Cobalamin by Attachment of the Fluorophore to Cobalt

Figure 2:
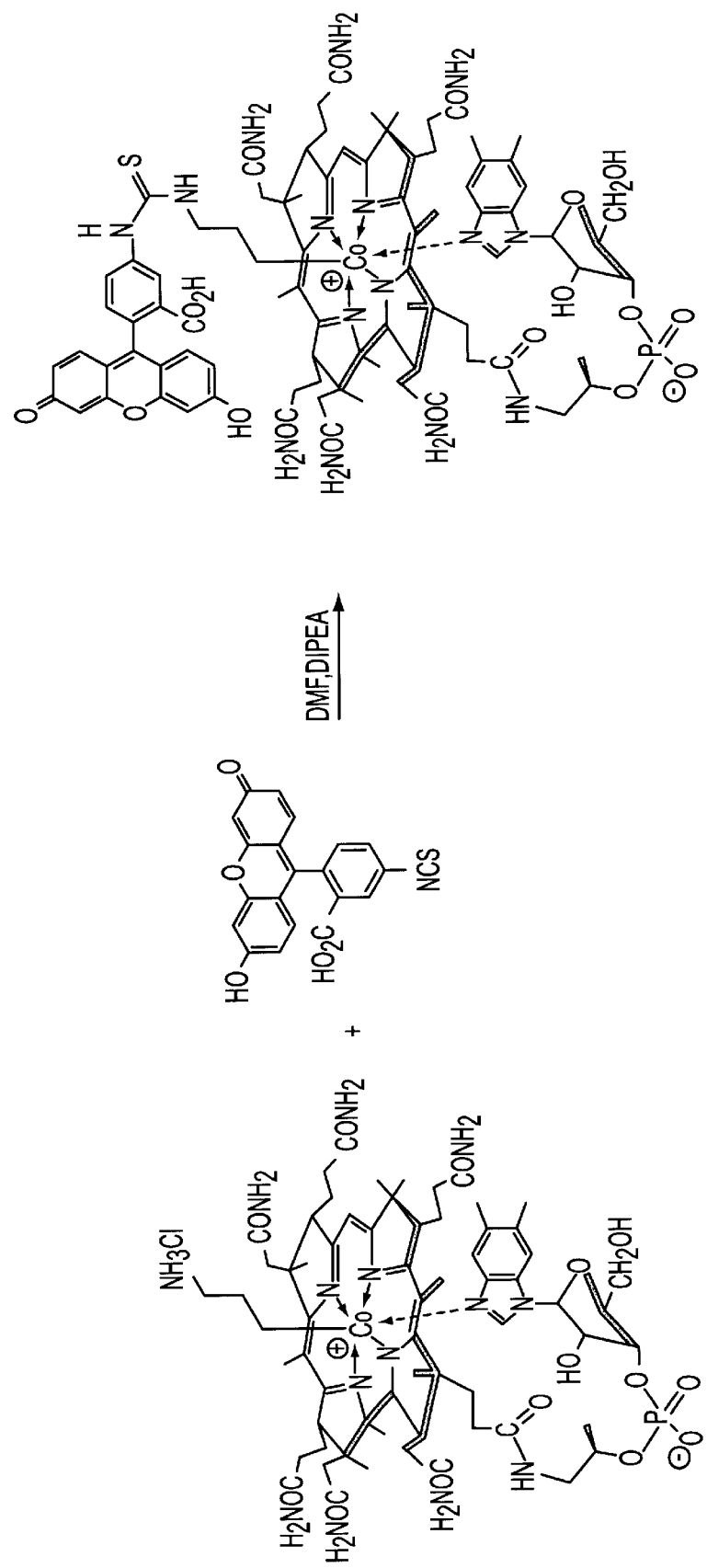
FIG. 2 shows the synthesis of one fluorescent cobalamin in accordance with the present invention.

As a visual indicator of cobalamin localization, five fluorescent analogues of cobalamin were prepared by covalently attaching fluorescein to cobalamin. Under green light illumination, the fluorescein molecule emits yellow light that can be detected by the dark-adapted eye to concentrations lower than 0.1 ppm. This emission enables the sensitive detection of cancer cells via epifluorescence microscopy, as well as by visual inspection. Each of the five fluorescent cobalamins exhibited intrinsic fluorescence. All of these compounds were synthesized by reacting aminopropyl chloride with cob(I)alamin to produce aminopropylcob(III)alamin in accordance with published techniques. In a subsequent step, aminopropylcob(III) alamin was reacted with a variety of fluorophore isothiocyanates (i.e. fluorescein isothiocyanate, "FITC") to produce the corresponding fluorophore that is linked to cobalamin through an aminopropyl linker (i.e. fluorescein-aminopropyl-cob(III)alamin) This latter reaction is shown in FIG. 2.

In a similar manner, fluorescent cobalamins were prepared in which the fluorophore is naphthofluorescein or Oregon Green. All the fluorescent cobalamins were found to retain high affinity for recombinant transcobalamin (rhTCII), thus allowing for a biological distribution similar to that observed fro naturally occurring cobalamin.

Example 2

Uptake of Cobalamin Analogues by Cancer Cells

A leukemic myeloblast preparation was made from a bone marrow aspirate of a 61-year old patient having acute myelogenous leukemia (AML) M1 (minimally mature myeloblasts in the FAB classification). Cells were treated three days post-harvest with a fluorescent cobalamin prepared as described in Example 1. Differential uptake of fluorescent cobalamin analogues, as determined by fluorescence microscopy or fluorescence flow cytometry, in normal and leukemic human bone marrow cells was found. The difference between normal marrow cells and leukemic myeloblasts (cancer cells) is particularly noteworthy, with no detectable cobalamin being taken up by normal cells. A bone marrow sample from a healthy individual showed no fluorescent labeling. Uptake of a doxorubicin-cobalamin conjugate, originally synthesized as a potential chemotherapeutic compound, was seen in P-388 murine leukemia cells and in HCT-116 human colon tumor cells. These results illustrate the uptake of fluorescent derivatives of cobalamin in leukemia and solid tumor cell lines.

Example 3

Preparation of Cyanocobalamin Monocarboxylic Acids

Figure 3:
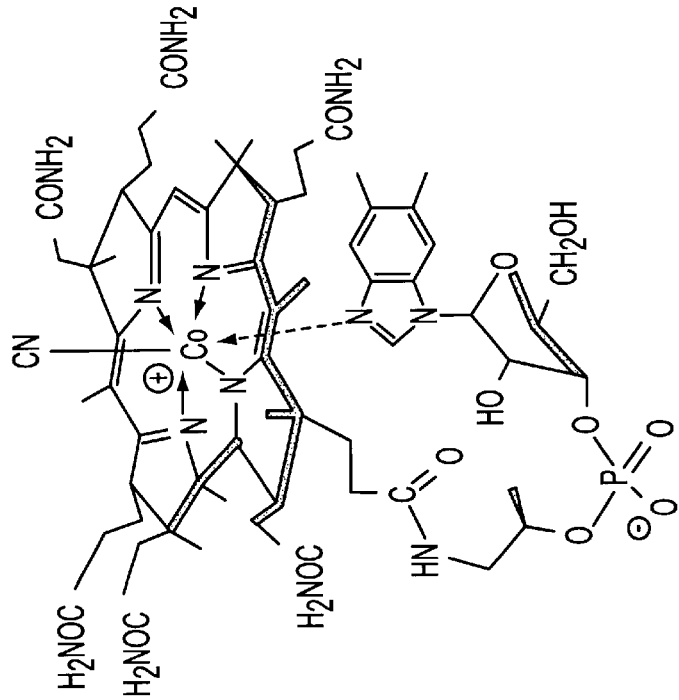
FIG. 3 shows the synthesis of cobalamin monocarboxylic acids.
Figure 3:
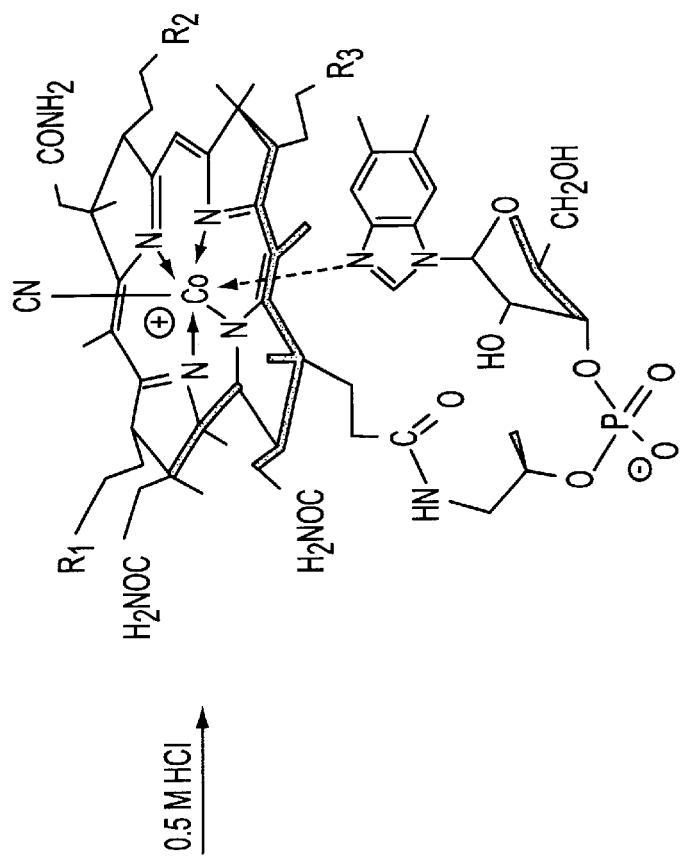

The b-, d-, and e-monocarboxylic acids were prepared by acid-catalyzed hydrolysis of cyanocobalamin. See FIG. 3. Briefly, cyanocobalamin (527.0 mg, 0.389 mmol) was placed into a 100 ml round bottom flask and dissolved in 40 ml of 0.5 M HCl. The flask was placed in a water bath at 50° C. and stirred for 4 hours. The reaction was monitored via HPLC (Waters, Inc. 3.9×300 mm DeltaPak 100 C-18 column) using the gradient tabulated in Table 1.

TABLE 1

| Time (min) | Flow Rate (ml/min) | 0.5 M $H_3PO_4$ (pH 3.0 w/ $NH_3OH$) | 9:1 $CH_3CN:H_2O$ |
| --- | --- | --- | --- |
| 0.0 | 2.0 | 90.0 | 10.0 |
| 2.0 | 2.0 | 90.0 | 10.0 |
| 18.0 | 2.0 | 83.7 | 16.3 |
| 23.0 | 2.0 | 30.0 | 70.0 |
| 25.0 | 2.0 | 30.0 | 70.0 |
| 30.0 | 2.0 | 90.0 | 10.0 |

After 4 hours the reaction was cooled to room temperature. The pH was adjusted to 7.0 with NaOH (10%) using a pH meter. The crude material was desalted using a C-18 SepPak column (Waters, Inc. P/N WAT023635) by first rinsing the column with 10 ml methanol followed by 15 ml deionized $H_2O$. The crude material was applied to the column via a syringe and rinsed with 10–15 ml deionized $H_2O$ followed by elution with 10 ml methanol. The methanol was removed via rotary evaporation and a red compound was obtained (5016-12-33).

The crude reaction mixture was dissolved in minimal deionized $H_2O$ and half of the solution was injected onto a semi-preparative HPLC (Waters, Inc. 25.0×300 mm 100 C-18 column) using the gradient calculated in Table 2.

TABLE 2

| Time (min) | Flow Rate (ml/min) | 0.5 M $H_3PO_4$ (pH 3.0 w/ $NH_3OH$) | 9:1 $CH_3CN:H_2O$ |
| --- | --- | --- | --- |
| 0.0 | 40.0 | 90.0 | 10.0 |
| 4.1 | 40.0 | 90.0 | 10.0 |
| 37.0 | 40.0 | 83.7 | 16.3 |

TABLE 2-continued

| Time (min) | Flow Rate (ml/min) | 0.5 M $H_3PO_4$ (pH 3.0 w/ $NH_3OH$) | 9:1 $CH_3CN:H_2O$ |
|---|---|---|---|
| 47.3 | 40.0 | 30.0 | 70.0 |
| 51.4 | 40.0 | 30.0 | 70.0 |
| 61.6 | 40.0 | 90.0 | 10.0 |

Peaks at 28.0 min (b-monocarboxylic acid, CBC-195), 30.1 min (d-monocarboxylic acid, CBC-226) and 34.6 min (e-monocarboxylic acid) were collected using large test tubes. The pure fractions were diluted 1:1 with deionized $H_2O$ and desalted in the same method above. In all cases, a red solid was obtained.

CBC-195 (b-monocarboxylic acid): In the two preparative runs, 74.8 mg of the b-monocarboxylic acid (14.4%) was isolated. A positive-ion electrospray mass spectrum ($ES^+$) was obtained that shows a M+1 peak (1356) and a M+22 peak (1378) as expected. The b-monocarboxylic acid (CBC-195) was obtained in an overall yield of 14%

CBC-226 (d-monocarboxylic acid): In the two prep. runs, 38.6 mg of the d-monocarboxylic acid (7.3%) was isolated. A positive-ion electrospray mass spectrum ($ES^+$) was obtained showing a M+1 peak (1356) and the corresponding M+Na peak (1378) as expected. The d-monocarboxylic acid (CBC-226) was obtained in an overall yield of 7%

The e-monocarboxylic acid was isolated, ~78 mg in an overall yield of 14%.

Example 4

Conjugation of CnCbl Acids with 1,12 Diaminododecane

Figure 4:
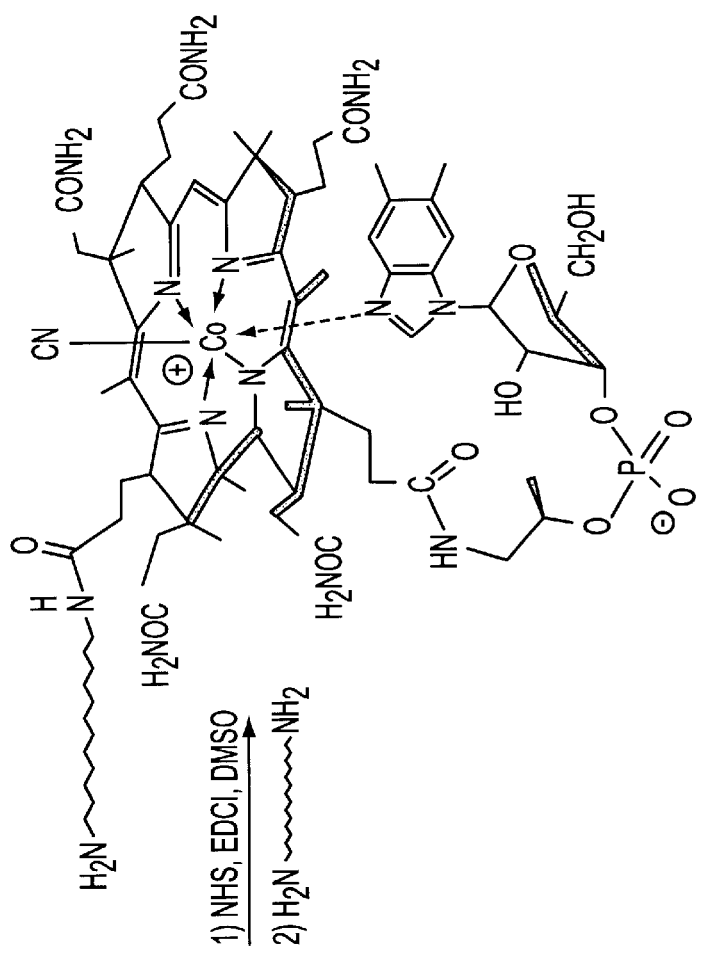
FIG. 4 shows the conjugation of cobalamin carboxylic acids with 1,12-diaminododecane.
Figure 4:
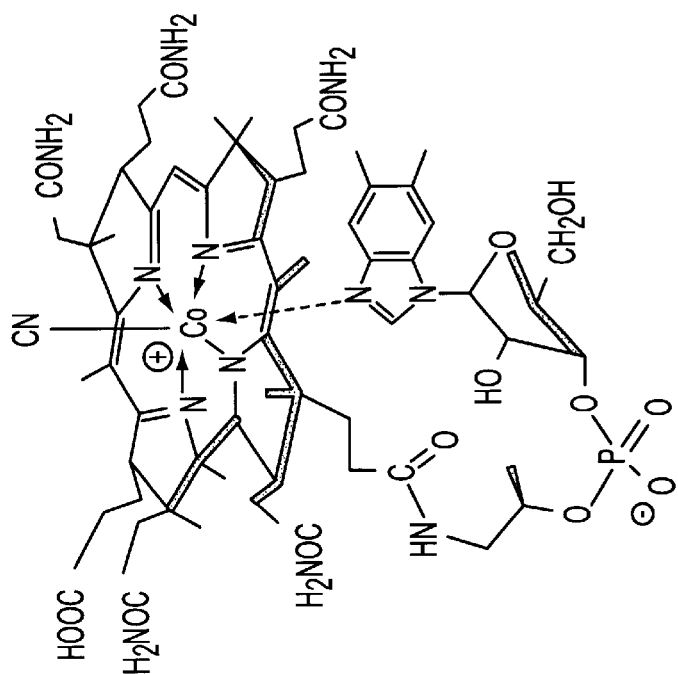

The b- and d-amines were prepared as shown in FIG. 4. CBC-195 (55.4 mg, 0.0408 mmol) was added to a small glass vial and dissolved in ~2.5 ml of DMSO followed by the addition of EDCIHCl (12 mg, 0.0626 mmol) and N-hydroxysuccinimide (NHS) (25 mg, 0.217 mmol). The reaction was stirred at room temperature overnight. From previous attempts, several equivalents of EDCI and NHS (a total of 6 equivalents) were required to drive the reaction to completion. After 24 hours, one additional equivalent of EDCI was added and the reaction was complete in a total of 26 hours. The reaction was monitored via HPLC using the gradient is Table 3. CBC-195 has a retention time of 9.07 min and the NHS-ester of CBC-195 has a retention time of 10.55 min.

TABLE 3

| Time (min) | Flow Rate (ml/min) | 0.5 M $H_3PO_4$ (pH 3.0 w/ $NH_3OH$) | 9:1 $CH_3CN:H_2O$ |
|---|---|---|---|
| 0.0 | 2.0 | 90.0 | 10.0 |
| 2.0 | 2.0 | 90.0 | 10.0 |
| 20.0 | 2.0 | 55.0 | 45.0 |
| 25.0 | 2.0 | 9.0 | 10.0 |

In a separate glass vial, 1,12-diaminododecane (81.8 mg, 0.408 mmol) was dissolved in ~2 ml DMSO. The above reaction mixture was added dropwise using a syringe pump at 4.0 ml/hr to minimize dimerization. The product was formed immediately and has a retention time of 14.56 min. The crude reaction mixture was added to 100 ml of 1:1 $CH_2Cl_2:Et_2O$ and a red precipitate formed. The red compound was filtered using a glass frit and washed with two 20 ml portions of $CH_2Cl_2$, two 20 ml portions of acetone, and finally by two 20 ml portions of $Et_2O$.

The crude reaction product was dissolved in a minimal amount of deionized $H_2O$ and the solution was injected onto a semi-preparative HPLC (Waters, Inc., 25.0×100 mm 100 C-18 column) using the gradient calculated in Table 4.

TABLE 4

| Time (min) | Flow Rate (ml/min) | 0.5 M $H_3PO_4$ (pH 3.0 w/ $NH_3OH$) | 9:1 $CH_3CN:H_2O$ |
|---|---|---|---|
| 0.0 | 40.0 | 90.0 | 10.0 |
| 2.0 | 40.0 | 90.0 | 10.0 |
| 13.7 | 40.0 | 55.0 | 45.0 |
| 17.1 | 40.0 | 90.0 | 10.0 |

The peak at 8.70 min (b-amine, CBC-208) was collected using large test tubes. The pure fractions were diluted 1:1 with distilled $H_2O$ and desalted using a C-18 SepPak column (Waters, Inc. P/N WAT023635) by first rinsing the column with 10 ml methanol followed by 15 ml deionized $H_2O$. The pure material was applied to the column via a syringe and rinsed with 10–15 ml deionized $H_2O$ followed by elution with 10 ml methanol. The methanol was removed via rotary evaporation and 6 mg of a red compound was obtained.

CBC-208 (b-amine): A total of 6.0 mg of the b-amine was isolated. A positive-ion electrospray mass spectrum ($ES^+$) was obtained that shows a M+1 peak (1538) and a M+23 peak (1560) as expected. CBC-208 was obtained in a yield of 9.5% after purification.

CBC-226 (d-amine): The d-monocarboxylic acid has an HPLC retention time of 9.32 min, the NHS-ester migrates at 10.96 min, and the d-amine (CBC-226) migrates at 14.93 min using the same HPLC gradient as in Table 3. A positive-ion electrospray mass spectrum ($ES^+$) was obtained of the crude material showing a M+1 peak (1538) and the corresponding M+Na peak (1560) as expected.

Example 5

Conjugation of CBC-208 and Fluorescein-5EX-NHS

Figure 5:
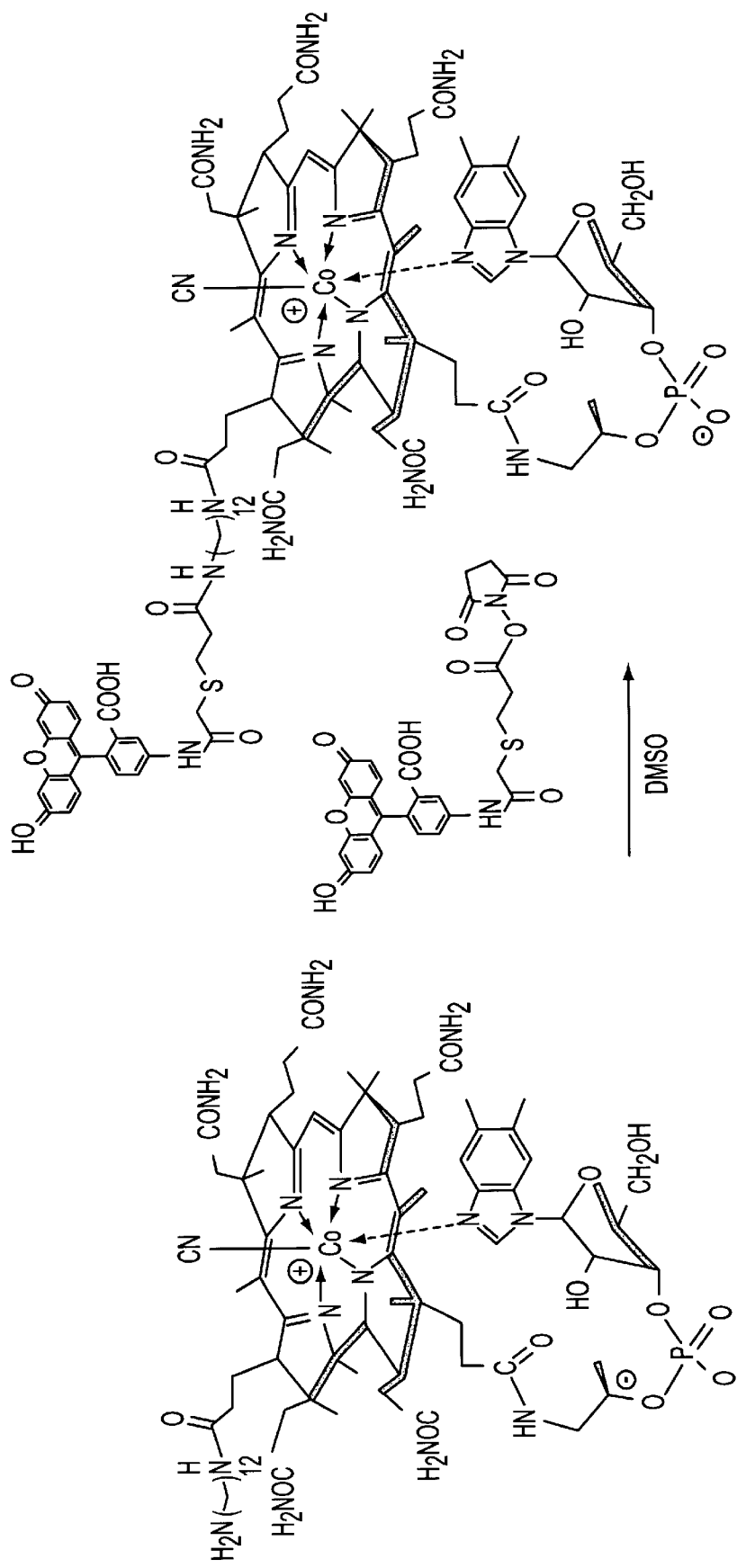
FIG. 5 shows conjugation of fluoroscein-5EX-NHS ester with the diaminododecane cobalamin derivative.

CBC-208 has been coupled to the fluorescein derivative fluorescein-5EX (available from Molecular Probes, Inc.) according to FIG. 5. CBC-208 (6.0 mg, 3.87 μmol) was added to a small glass vial and dissolved in ~0.5 ml of DMSO followed by the addition of fluorescein-5EX-NHS (2.5 mg, 4.23 μmol). The reaction was allowed to stir at room temperature overnight. The reaction was monitored via HPLC using the method in Table 5.

TABLE 5

| Time (min) | Flow Rate (ml/min) | 0.5 M $H_3PO_4$ (pH 3.0 w/ $NH_3OH$) | 9:1 $CH_3CN:H_2O$ |
|---|---|---|---|
| 0.0 | 2.0 | 90.0 | 10.0 |
| 2.0 | 2.0 | 90.0 | 10.0 |
| 10.0 | 2.0 | 65.0 | 35.0 |
| 15.0 | 2.0 | 5.0 | 95.0 |
| 28 | 2.0 | 90.0 | 10.0 |

The reaction proceeded very quickly initially forming the desired product after only 10 minutes of contact. CBC-208 has a retention time of 11.47 min and the product (CBC-123)

has a retention time of 14.24 min. With the addition of another equivalent of the fluorescein compound the reaction goes to completion and the crude mixture is 88% pure.

HPLC analysis of the starting material fluorescein-5EX-NHS shows that it is only 75% pure, which explains why an additional equivalent was necessary in order to drive the reaction to completion.

CBC-123 (b-fluorescein cobalamin derivative): This compound is nearly 90% pure as the crude isolate from the synthesis, with the majority of the impurity being unreacted CBC-208. A positive-ion electrospray mass spectrum ($ES^+$) was obtained of the crude material showing a M+1 peak (2013) and the corresponding M+Na peak (2035). The yield before purification is 22%.

Figure 6:
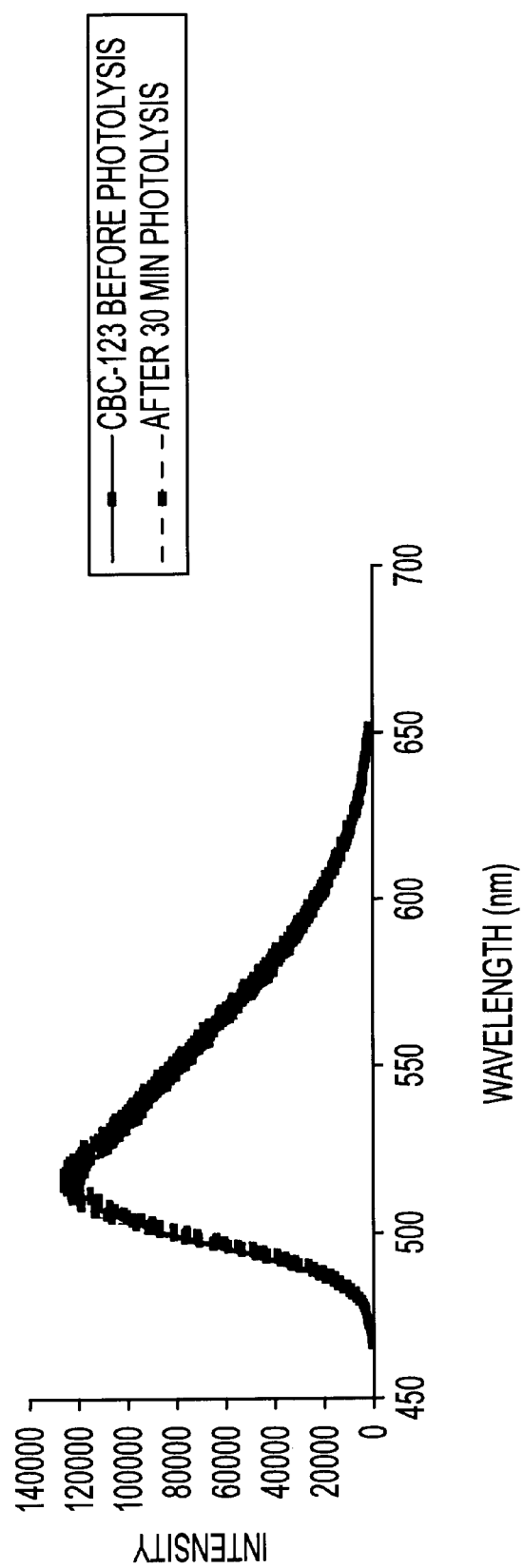
FIG. 6 shows the fluorescence emission spectrum of fluorescein-5EX-b-cobalamin derivative CBC-123.

A fluorescence spectrum of this compound was taken of the crude compound before and after photolysis with excitation at 350 nm (see FIG. 6). There is no significant change in fluorescence before and after photolysis suggesting that the compound is photostable and is overtly fluorescent and does not exhibit diminished fluorescence from the proximity of cobalamin.

Example 6

Ex vivo Examination of Breast Tumor Tissue via Microscopy

Samples of malignant and benign tumors, including tumors of the breast, with attached normal margin tissue are excised from patients. These samples are taken with approval of the University of Utah Institutional Review Board (IRB) and the Huntsman Cancer Institute Clinical Cancer Investigation Committee (CCIC). The live tissue samples are incubated with one of the fluorescent cobalamin derivatives prepared above for 4–6 hours. Thin tissue sections of each sample are prepared with a cryomicrotome and the amount of fluorescent marker is quantified in normal and cancerous tissue by epifluorescence microscopy. Corresponding tissue sections are stained with hematoxylin/eosin (H&E) stain for evaluation by an anatomical pathologist. The interface between normal and cancerous cells is examined carefully. Cells from the interior of the tumor are also examined for uptake of fluorescent marker, since cells within hypoxic regions of a tumor often have decreased metabolism.

More specifically, Minimum Essential Medium, alpha modification (α-MEM; 7.5% newborn calf serum, 2.5% fetal bovine serum, 0.2% nystatin, 2.5% penicillin/streptomycin, pH7.2; Sigma) was prepared and aliquoted (10 mL) into sterile 25 mL screw top tissue culture flasks. The media was brought to 37° C., and tissue samples were incubated with fluorescently labeled cobalamins (50 nM; cobalamin-Oregon Green and cobalamin-naphthofluorescein conjugates of Example 1 and cobalamin-fluorescein conjugate of Example 5) and recombinant human TCII (50 pM) in α-MEM for 3 hours. Human breast tissue samples were procured under an IRM-approved protocol. The tissue was removed from the flask, washed with Dulbecco's Phosphate Buffered Saline (DPBS; Sigma), and mounted on a brass plate at −20° C. with OCT compound (Shandon) for frozen section slicing. Tissue was sliced (4–6 µm sections) in a CTD Harris cryostat at −20° C. Thin tissue sections were pulled back with a small artist brush and fixed to a microscope slide with 100% ethanol. Slides were stained using a standard hematoxylin staining procedure: 95% ethanol, 20 seconds; water, 5 seconds; hematoxylin (Fisher), 45 seconds; water, 5 seconds; bluing solution (tap water), 10 seconds; 95% ethanol, 10 seconds; 100% ethanol, 10 seconds; xylene, 10 seconds; and xylene, 10 seconds. Slides were evaluated by phase contrast and epifluorescence microscopy at 10×, 60× and 100× magnification.

3-[4,5-Dimethylthiazol-2-yl]-2,5-diphenyltetrazolium thiazolyl bromide (MTT; Sigma) was used to qualitatively determine the metabolic competency of the tissue after 3 hours incubation time with fluorescent cobalamin. A portion of the tissue was removed from the media, washed with DPBS, and immersed in MTT (2 mL; 2.5 mg/mL). This tissue was incubated for 3 hours under a 5% CO2 atmosphere at 37° C. During this incubation period, viable cells in the tissue sample reduced the MTT dye to purple formazan by succinate dehydrogenase activity (Celis and Celis, 1998). The tissue was washed with DPBS and prepared according to the cryomicrotome procedure outlined above to ensure the metabolic competency of the tissue.

The fluorescent cobalamin bioconjugates accumulated to some extent in both neoplastic and healthy breast tissue, with the neoplastic breast tissue sequestering more fluorescent cobalamin than healthy breast tissue. The amount of fluorescent cobalamin sequestered by healthy breast tissue is larger than expected, but it is believed that it is due to non-specific binding to structures within connective tissue rather than to significant internalization by healthy cells.

Example 7

Ex vivo Examination of Cancer Cells in Lymph Nodes

Excised lymph nodes with metastatic disease are removed from patients and incubated for 4–8 hours with one of the fluorescent cobalamin derivatives prepared above. Each lymph node is sectioned and examined microscopically for transport of the fluorescent cobalamin into cancer cells. This experiment showed the ability of metastatic cells within lymph nodes to take up sufficient fluorescent cobalamin for imaging and visualization.

Example 8

Use of Fluorescent Cobalamin to Determine Whether a Patient Will Respond Favorably to Chemotherapy with a Cobalamin-Based Therapeutic Bioconjugate A bone marrow aspirate or a peripheral blood sample from a patient with leukemia is incubated with a fluorescent cobalamin conjugate. After 4–8 hours, bone marrow aspirate or peripheral blood sample is washed to remove unincorporated fluorescent label and the cell sample subjected to qualitative or quantitative fluorescence analysis by epifluorescence microscopy or flow cytometry. Cells that have taken up a significant amount of fluorescent cobalamin exhibit a brighter fluorescence. The uptake of a significant amount of fluorescent cobalamin indicates that the type of leukemia the patient has will respond favorably to treatment with a cobalamin-based therapeutic. A bone marrow aspirate or a peripheral blood sample that does not show significant fluorescence after treatment with a fluorescent cobalamin conjugate indicates that the patient will not respond favorably to a cobalamin-based therapeutic conjugate. A similar approach can be applied to solid tumors. In this case, a portion of the excised tumor tissue is incubated with the fluorescent cobalamin conjugate and, after about 4–8 hours, fluorescence in the tumor tissue is quantified. The greater fluorescence exhibited by the tumor tissue, the greater the likelihood that the cancer will respond favorably to treatment with a cobalamin-based chemotherapeutic.

Example 9

Synthesis of CobalaFluor Y

General Desalting Procedure. All cobalamins were desalted with a 10 g C-18 SepPak (Waters, Inc.) by conditioning the cartridge with two column volumes of methanol and three column volumes of deionized water. The cobalamin was applied to the column, washed with three column volumes of deionized water, and eluted with methanol (10 mL). The methanol was removed via rotary evaporation and the product was dried by lyophylization.

Preparation of cyanocobalamin-b-monocarboxylic acid. Cyanocobalamin-b-monocarboxylic acid was prepared according to a modified published protocol (Anton et al., 1980). In brief, CnCbl (3.5 g, 2.6 mmol) was dissolved in 350 mL of 1.0 M HCl. The reaction was heated to 37° C. for 4 h and monitored via reverse phase HPLC. The crude material was desalted and could then be purified via semi-prep HPLC. However, since the crude reaction mixture contained over 45% cyanocobalamin (via HPLC) an ion exchange column was used separate the unreacted cyanocobalamin. Crude material was dissolved in ddH$_2$O and applied to a 2.5×30 cm Dowex AG-X1 (acetate form) column. CNCbl was eluted from the column with deionized water. The three monocarboxylic acids were then eluted with 0.04 M sodium acetate (pH 4) and were further purified via semi-preparative HPLC. The b-monocarboxylic acid was isolated (10% overall yield) in 97% purity by analytical HPLC; ES$^+$ MS: (1:1 H$_2$O:CH$_3$CN) M+H=1356.3 (calc. C$_{63}$H$_{88}$CoN$_{13}$O$_{15}$P=1356.5), M+Na$^{+=}$1378.4 (calc. C$_{63}$H$_{88}$CoN$_{13}$O$_{15}$PNa=1378.5). Both the d- and e-monocarboxylic acids were also isolated in 4% and 7% overall yields respectively.

Analytical HPLC method for cyanocobalamin-b-monocarboxylic acid: Analytical chromatography was carried out at a flow rate of 2 mL/min using a Waters DeltaPak C-18 300×3.9 mm column. After an initial 2 min isocratic flow of 90% solution A (0.05 M phosphate buffer, pH 3.0) and 10% solution B (9:1 acetonitrile and water), a 16 min linear gradient to 83.7% A and 16.3% B eluted the desired b-monocarboxylic derivative with a retention time of 15.7 min. The d-monocarboxylic acid had a retention time of 16.9 min and the e-monocarboxylic acid had a retention time of 19.5 min.

Semi-preparative HPLC for cyanocobalamin-b-monocarboxylic acid: Chromatography was carried out at a flow rate of 40 mL/min using a Waters DeltaPak C-18 2.5×30 cm semi-preparative column. After a 4.1 min isocratic flow of 90% solution A (0.05 M phosphate buffer pH 3.0) and 10% solution B (9:1 acetonitrile and water), a 32.9 min linear gradient to 83.7% A and 16.3% B eluted the cobalamin derivative. The retention times of the three CNCbl-monocarboxylic acids were as follows: the b-monocarboxylic acid eluted at 23.1 min, the d-monocarboxylic acid at 26.6 min and the e-monocarboxylic acid at 32.1 min.

Synthesis of cyanocobalamin-b-(5-aminopentylamide). Cyanocobalamin-b-monocarboxylic acid 1 (50 mg, 0.037 mmol) was dissolved in a dry 10 mL round bottom flask with EDCI (71 mg, 0.37 mmol) and NHS (25 mg, 0.22 mmol). The flask was degassed by flushing with nitrogen for 5 min. Dimethylsulfoxide (5 mL) was added via syringe and the reaction mixture stirred for 6 h. This mixture was removed from the round bottom flask using a gas-tight syringe, and 1,5-diaminopentane (43 µL, 0.37 mmol) was placed in the flask. The Cbl mixture was added dropwise to the 1,5-diaminopentane over a period of 5 min to minimize formation of 2:1 adduct. Reverse phase HPLC was used to monitor the reaction. When starting material was consumed, a solution of 1:1 CH$_2$Cl$_2$:diethylether (60 mL) precipitated the cobalamins. The resultant solid was filtered on a medium frit filter, washed with diethylether (2×10 mL), and eluted from the filter with methanol. The crude mixture was diluted with an equal volume of water and injected onto a semi-preparative column to purify the cyanocobalamin-b-(5-aminopentylamide) 2. A fraction containing the desired product was desalted as described above and dried by rotary evaporation. Cyanocobalamin-b-(5-aminopentylamide) was obtained: 70% yield; 98% pure by analytical HPLC; ES$^+$ MS: (1:1 H$_2$O:CH$_3$CN) M+H=1440.5 (calc. C$_{68}$H$_{100}$CoN$_{15}$O$_{14}$P=1440.7), M+Na$^+$=1462.4 (calc. C$_{68}$H$_{100}$CoN$_{15}$O$_{14}$PNa=1462.6); $\epsilon_{362\ nm}$=19500 M$^{-1}$ cm$^{-1}$ in H$_2$O.

Analytical HPLC method for cyanocobalamin-b-(5-aminopentylamide) 2: Analytical chromatography was carried out at a flow rate of 2 mL/min on a Waters DeltaPak C-18 300×3.9 mm column. After a 2 min isocratic flow of 95% solution A (0.05 M phosphate buffer, pH 3.0) and 5% solution B (9:1 acetonitrile and water), a 16.4 min linear gradient to 70% A and 30% B eluted the compound of interest at 11.8 min.

Semi-preparative HPLC for cyanocobalamin-b-(5-aminopentylamide) 2: Semi-preparative chromatography was carried out at 40 mL/min using a Waters DeltaPak C-18 25×30 cm semi-preparative column. After an isocratic flow of 95% solution A (0.05 M phosphate buffer pH 3.0) and 5% solution B (9:1 acetonitrile and water) for 4.1 min, an 18 min. linear gradient to 70% A and 30% B eluted the desired product.

Figure 7:
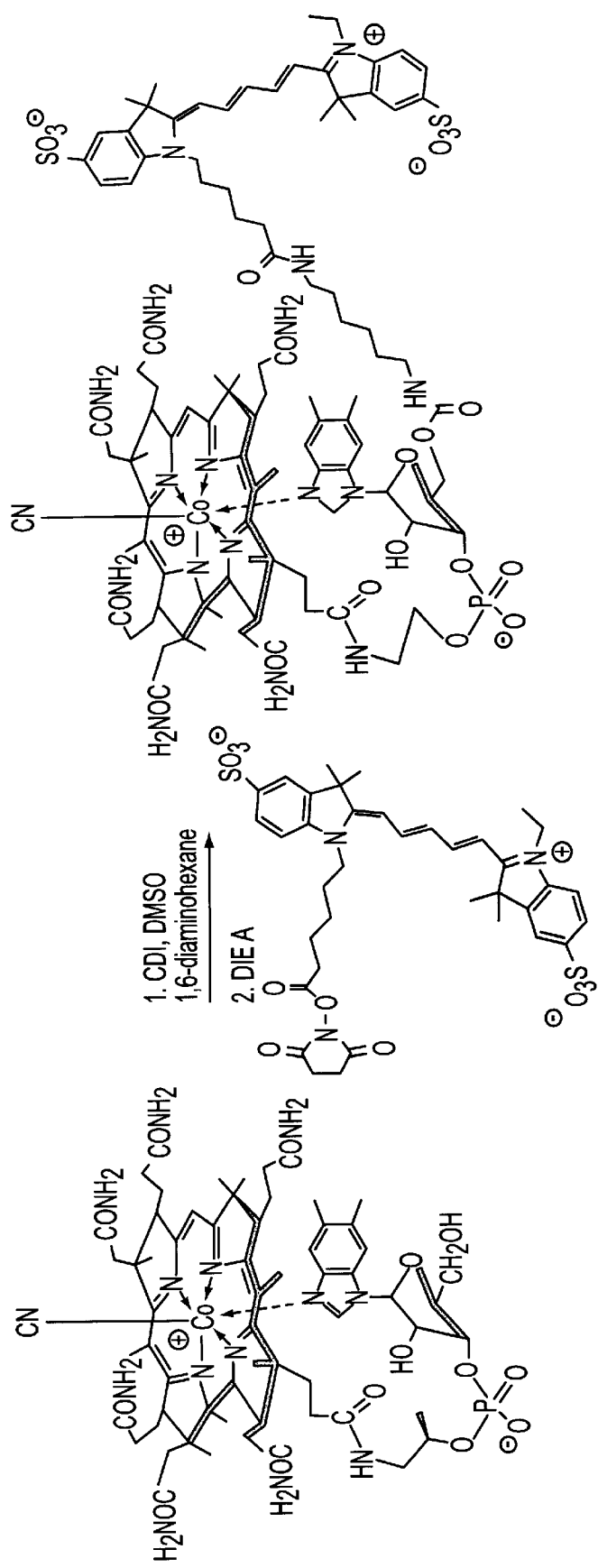
FIG. 7 shows the synthesis of CobalaFluor Y.
Figure 8:
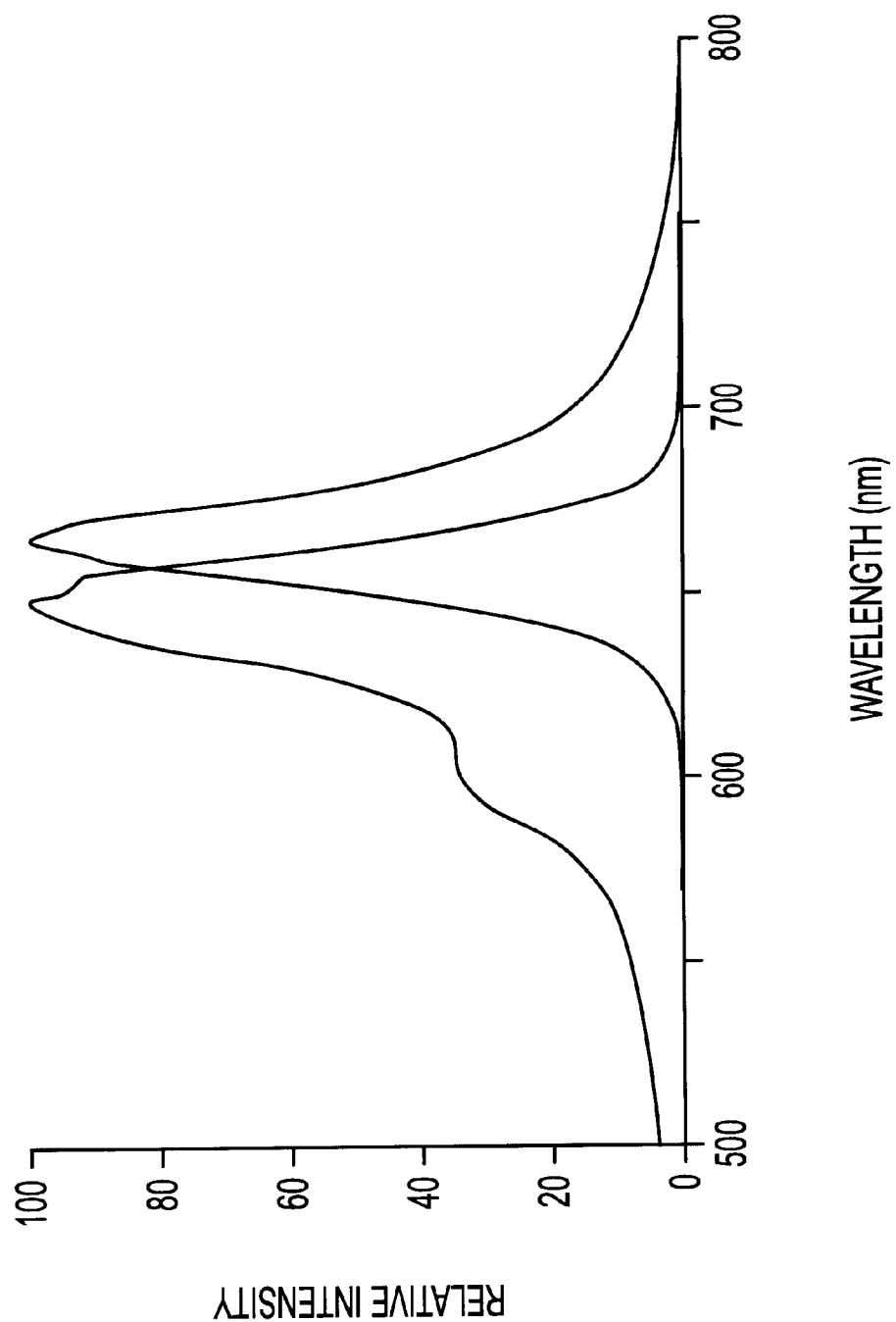
FIG. 8 shows fluorescence emission spectrum of CobalaFluor Y (Cy5 CobalaFluor).

Synthesis of CobalaFluor Y (Cy5-Cobalamin=Cy5-Cbl= Cy5 CobalaFluor). This synthesis is shown in FIG. 7. Briefly, cyanocobalamin-ribose-5'-O-(6-aminohexylamide) was prepared using cyanocobalamin (Sigma Chemical Co.) according to a published protocol (McEwan et al., 1999). Cobalamins were precipitated using 2:1 diethylether:methylene chloride (50 mL) and also washed with this solvent mixture (2×10 mL). The reaction was monitored and the product purified via reverse phase HPLC. The product was desalted according to standard procedure. Cyanocobalamin-ribose5'-O-(6-aminohexylamide) (20 mg, 0.013 mmol) was placed in a dry 10 mL round bottom flask and degassed by flushing with nitrogen for 5 min. Dimethylsulfoxide (1 mL) was added via syringe to dissolve the cobalamin. Cy5 succinimidyl ester (10 mg, 0.013 mmol; Amersham Pharmacia) and DIPEA (15 µL, 0.13) were added to the flask and the reaction mixture stirred for 1 h. Reverse phase HPLC was used to monitor the reaction. When starting material was consumed, a solution of 2:1 diethylether:CH$_2$Cl$_2$ (50 mL) precipitated the cobalamins. The resultant solid was filtered on a fine frit filter, washed with the diethylether and CH$_2$Cl$_2$ mixture (2×10 mL), and eluted from the filter with methanol. The crude mixture was injected onto a semi-preparative column to purify CobalaFluor Y and desalted according to standard procedure. FIG. 8 shows fluorescence emission spectrum of CobalaFluor Y.

Analytical HPLC method for cyanocobalamin-ribose-5'-O-(6-aminohexylamide): Analytical chromatography was carried out at a flow rate of 2 mL/min using a Waters DeltaPak C-18 300×3.9 mm column. After an initial 2 min isocratic flow of 95% solution A (0.05 M phosphate buffer, pH 3.0) and 5% solution B (9:1 acetonitrile and water), an 18 min linear gradient to 70% A and 30% B eluted the desired cyanocobalamin-ribose-5'-O-(6-aminohexylamide) with a retention time of 12.5 min.

Semi-preparative HPLC for cyanocobalamin-ribose-5'-O-(6-aminohexylamide): Chromatography was carried out at a flow rate of 40 mL/min using a Waters DeltaPak C-18 2.5×30 cm semi-preparative column. After a 4.1 min isocratic flow of 95% solution A (0.05 M phosphate buffer pH 3.0) and 5% solution B (9:1 acetonitrile and water), a 27.4 min linear gradient to 70% A and 30% B eluted the cobalamin derivative. The retention time of the desired cyanocobalamin-ribose-5'-O-(6-aminohexylamide) was 15.5 min.

Analytical HPLC method for CobalaFluor Y: Analytical chromatography was carried out at a flow rate of 2 mL/min on a Waters DeltaPak C-18 300×3.9 mm column. After a 2 min isocratic flow of 95% solution A (0.01 M TEA buffer, pH 7.0) and 5% solution B (9:1 acetonitrile and water), a 16.4 min linear gradient to 45% A and 55% B eluted CobalaFluor Y at 13.6 min.

Semi-preparative HPLC for CobalaFluor Y: Semi-preparative chromatography was carried out at 20 mL/min using a Waters DeltaPak C-18 25×30 cm semi-preparative column. After an isocratic flow of 95% solution A (0.01 M TEA buffer, pH 7.0) and 5% solution B (9:1 acetonitrile and water) for 2 min, a 27.4 min linear gradient to 70% A and 30% B eluted the desired product at 12.2 min.

Example 10

Competition Assay

Materials. Cobalamins, porcine non-intrinsic factor (50:1 mixture of HC and IF), and porcine intrinsic factor were purchased from Sigma Chemical Co. HPLC traces were obtained using a Waters Delta 600 system equipped with a Waters 2487 dual wavelength absorbance detector. BIACORE 2000 and 3000 (BIACORE AB) instruments were used for surface plasmon resonance biosensor analysis.

Figure 9:
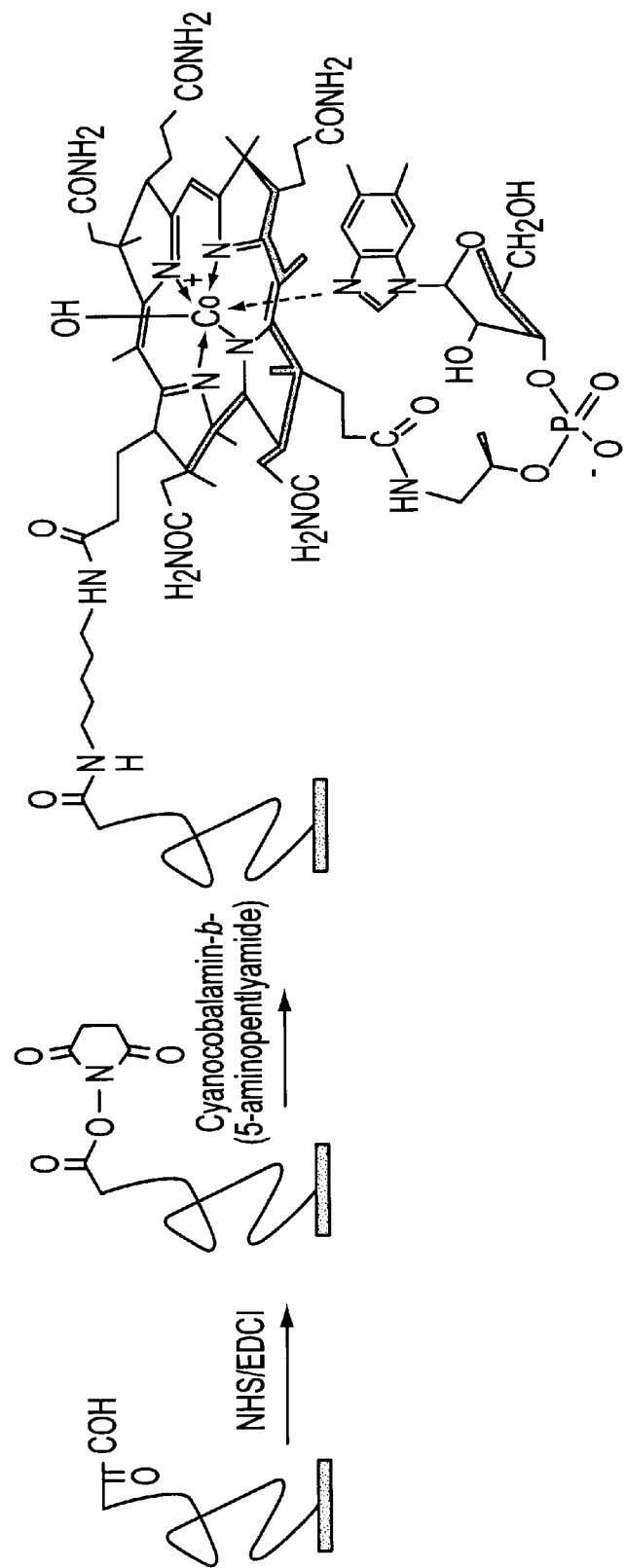
FIG. 9 shows the immobilization of a cobalamin analog on a CM5 BIAcore chip.

Immobilization of CNCbl-b-(5-aminopentylamide). All SPR studies were carried out on a BIACORE 2000 optical biosensor. Carboxymethyl dextran surfaces in the flow cells of a standard CM5 sensor chip (BIACORE AB) were activated by flowing a mixture of 0.1 M EDCI and 0.025 M NHS at 37° C. through the chip at 20 µL/min for 15 min. CNCbl-b-(5-aminopentylamide) 2, diluted in 10 mM sodium acetate at pH 4.5, was immobilized on three flow cells of the chip as shown in FIG. 9. High density sensor surfaces (500–700 RU) were created by pulsing the Cbl analog over the flow cells for 40 min at a rate of 2 µL/min. The remaining binding sites on the surface of the chip in all four flow cells were blocked with 1.0 M ethanolamine, pH 8.5, for 16 min at 5 µL/min. Flow cell 3 was used as a reference surface to subtract non-specific binding and instrument noise.

Protein Standard Curve. All standard curve and competition assays were performed using HBS running buffer (150 mM NaCl, 10 mM HEPES, pH 7.5, 3.4 mM EDTA, 1 mg/mL BSA, and 0.005% P20 surfactant) at 30° C. Calibration curves for rhTCII, NIF, and IF binding CNCbl-b-(5-aminopentylamide) were generated as follows. Stock solutions of each protein (15.6–500 pM) diluted in HBS buffer were injected through the flow cells at 20 µL/min for 10 min to analyze binding. The bound protein was removed with 8 M urea, 0.125% SDS, and running buffer. Each protein sample was analyzed in duplicate.

Determination of the Apparent Solution Equilibrium Dissociation Constants. The binding of rhTCII, NIF, and IF to various cobalamin analogs were analyzed by a solution competition binding assay (Nieba et al., 1996). Analog concentrations ranging from 0.01–100 nM were incubated in equal volume with 200 pM rhTCII, 200 pM NIF, or 500 pM IF. Binding data were generated by injecting an aliquot of the competing Cbl analog and protein at a rate of 20 µL/min for 10 min at 30° C., and the surface was regenerated with pulses of 8 M urea, 0.125% SDS, and buffer. The competition assay for each cobalamin was performed in duplicate.

Figure 10:
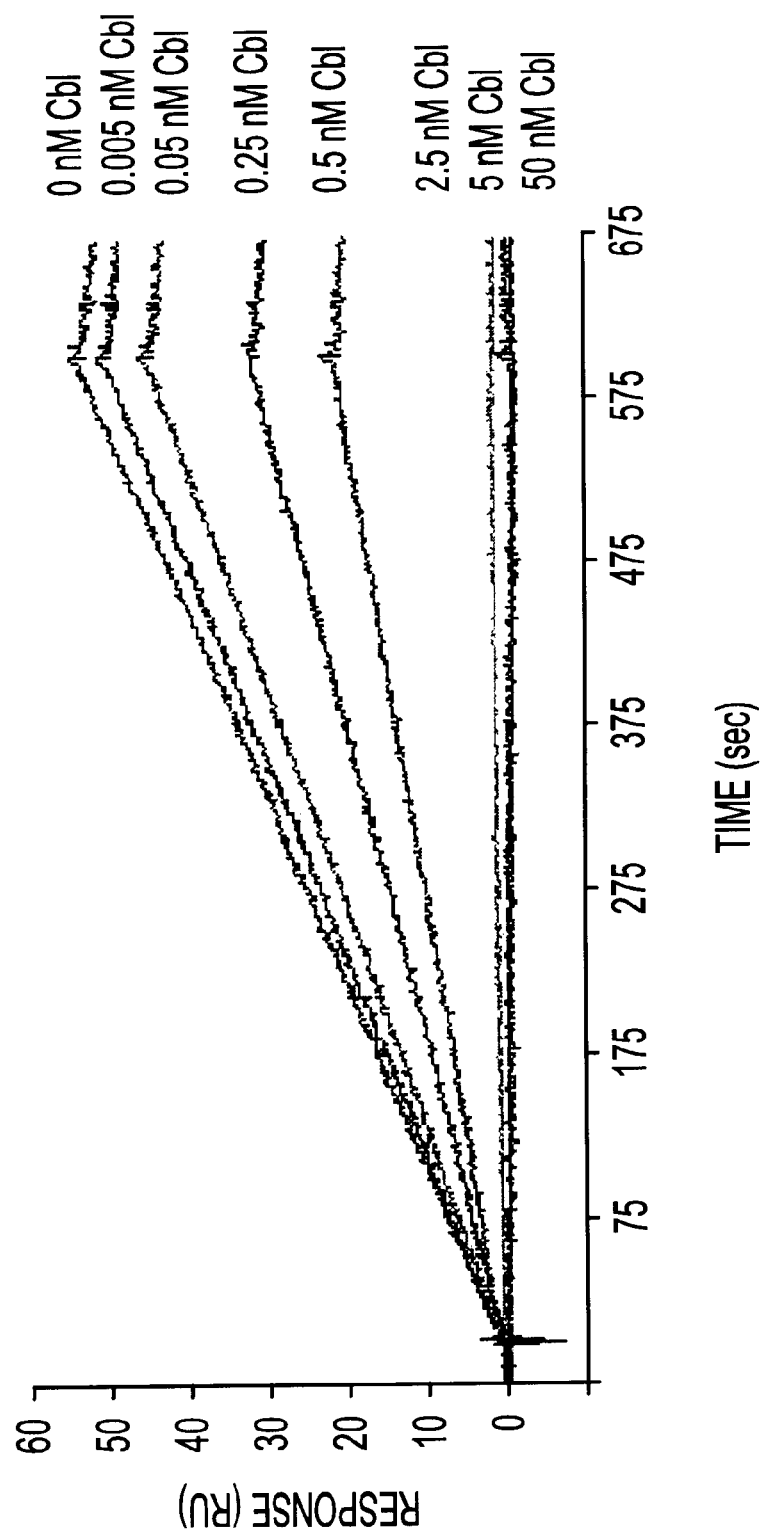
FIG. 10 shows a competition assay sensorgram.
Figure 11:
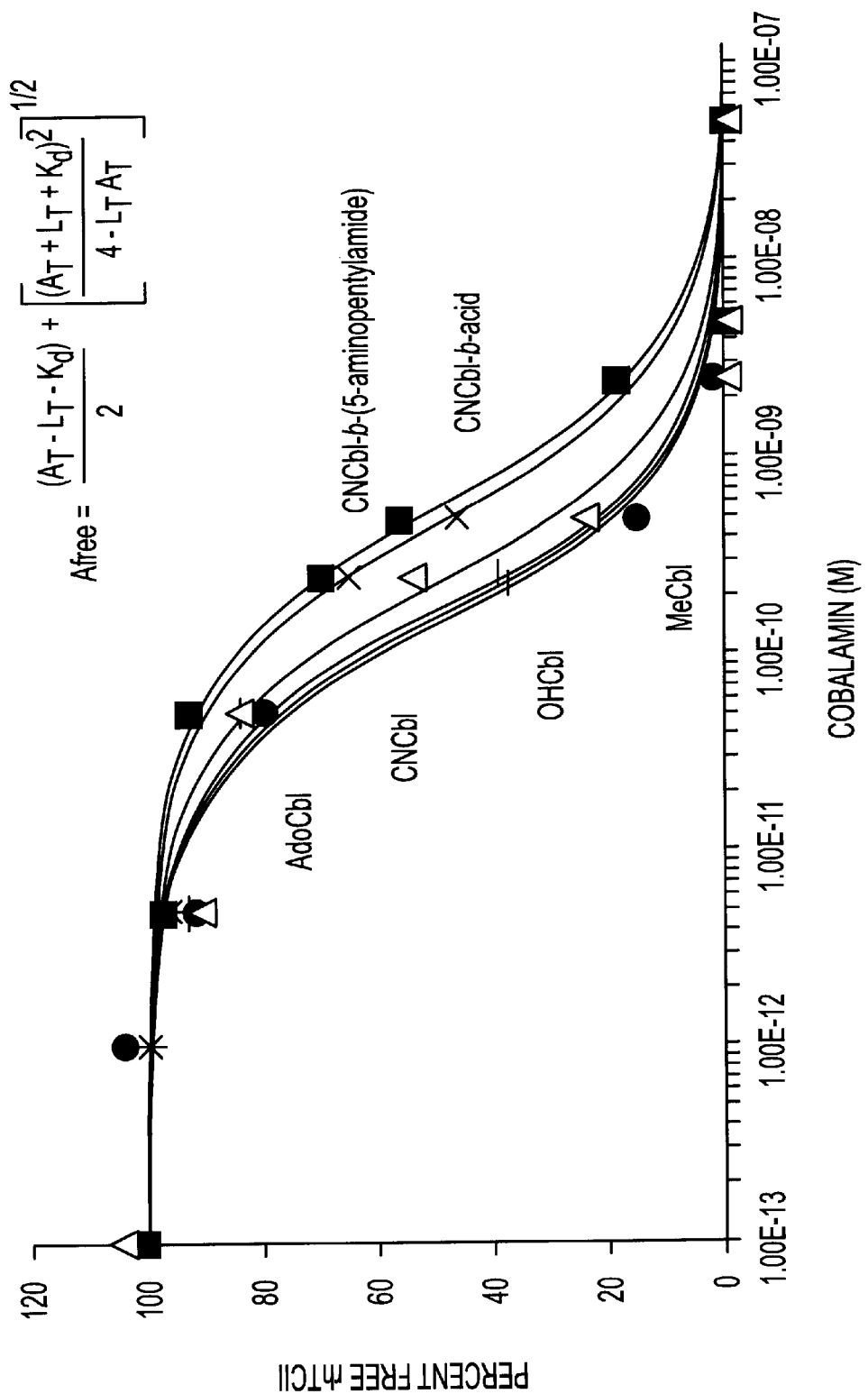
FIG. 11 shows the competition of cobalamin for TCII binding.
Figure 12C:
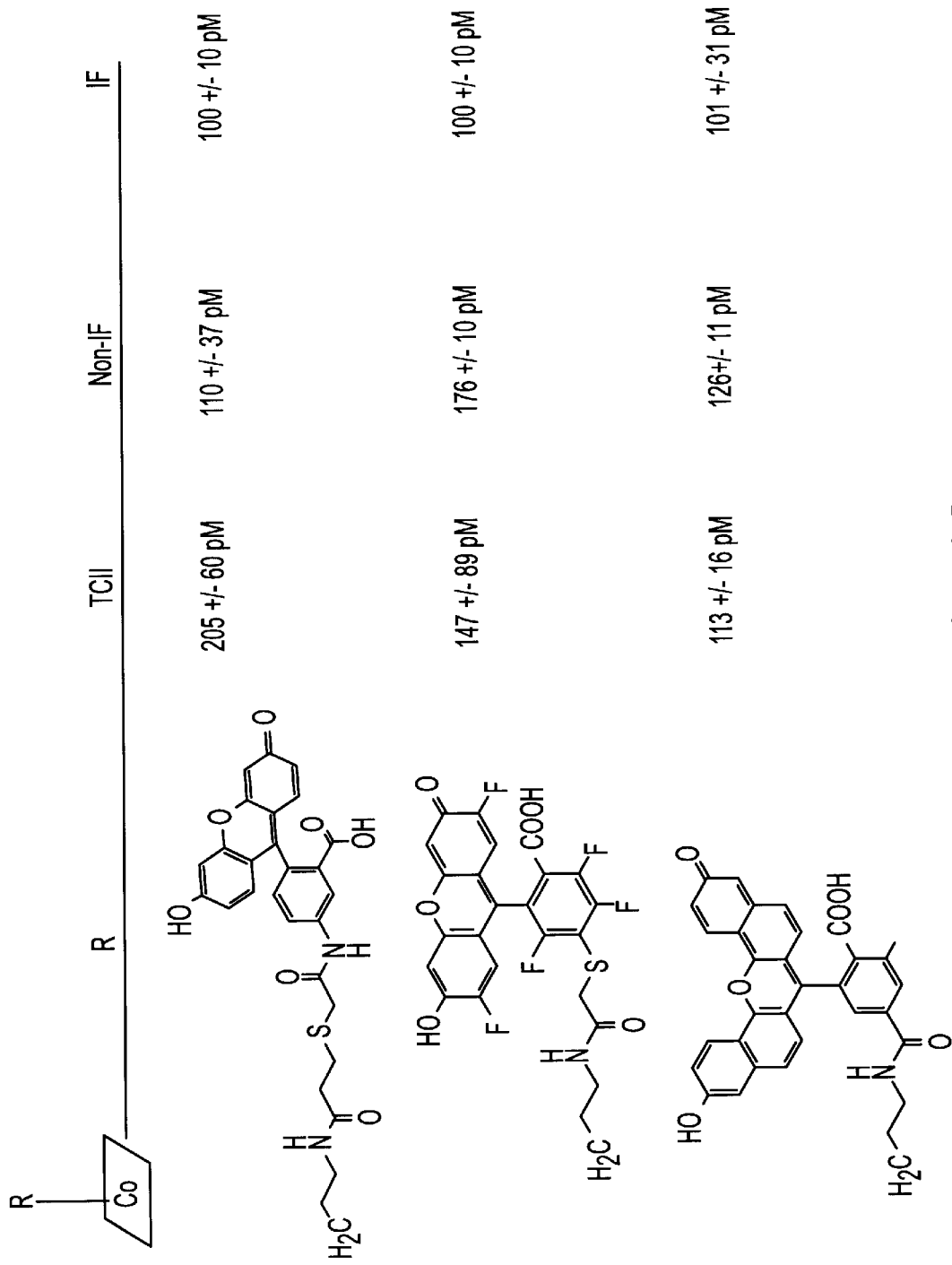

Data Analysis. Biosensor data were prepared for analysis by subtracting the binding responses observed from the reference surface and subtracting an average of three blank injections (Myszka, 1999). Data from the competition assays were fitted with non-linear least squares regression analysis supplied with BIA evaluations 3.0 software. FIG. 10 shows the competition assay sensogram. FIG. 11 shows the competition of cobalamin for TCII binding. The binding data is shown in FIGS. 12A–12C. These results demonstrate that cobalamin analogs are recognized by cobalamin transport proteins (transcobalamin, haptocorrin and intrinsic factor) with high affinity. This recognition has also been shown by surface plasmon resonance. The attachment of large molecules to cobalamin does not appear to affect protein binding.

Example 11

Animal Model Study

Figure 13:
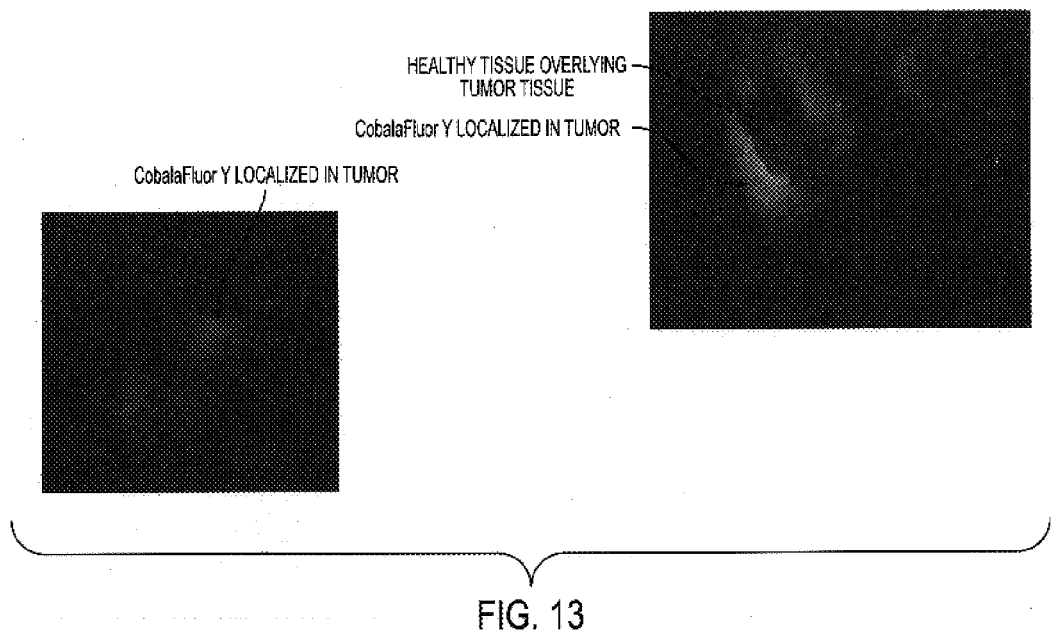
FIG. 13 shows tumor imaging in animal models.

In Vivo Uptake in Mice with Tumors. Tumors are implanted in mice by implanting 1×10⁶ RD995 tumor cells subcutaneously on the right hind leg of female mice. The mouse tumor cell line was propagated in vitro. Six weeks after implantation of the cells, a 10 mm tumor was visible. At this time, the mice were given a retro-orbital intravenous injection of 2.2 µg of CobalaFluor Y dissolved in sterile saline. At 6 hours post-injection, the mouse was sedated with the inhalation halothane. The tumor was sliced open and irradiated with a 633 nm HeNe laser. A tumor on a mouse was also analyzed at 54 hours post-injection of CobalaFluor Y using the HeNe laser. The mice were disected so internal organs and healthy tissue could be analyzed. The results are shown in FIG. 13, which demonstrates that fluorescently labeled cobalamin localizes in tumor tissue in mice.

Example 12

Tissue Uptake Study

Figure 14:
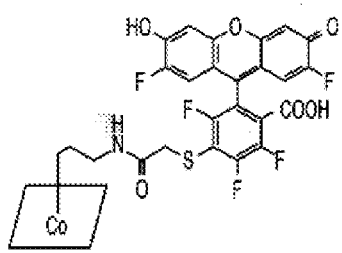
FIG. 14 shows tumor imaging in neoplastic breast tissue.
Figure 14:
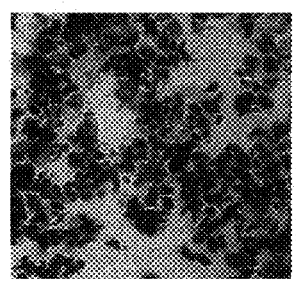
Figure 14:
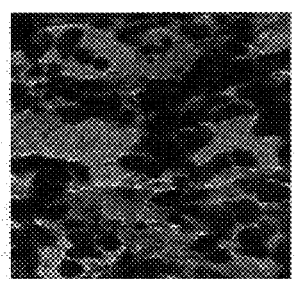
Figure 14:
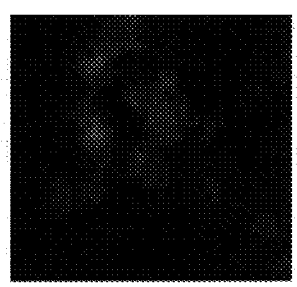
Figure 14:
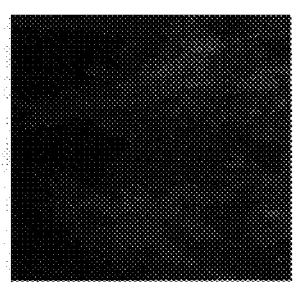
Figure 15:
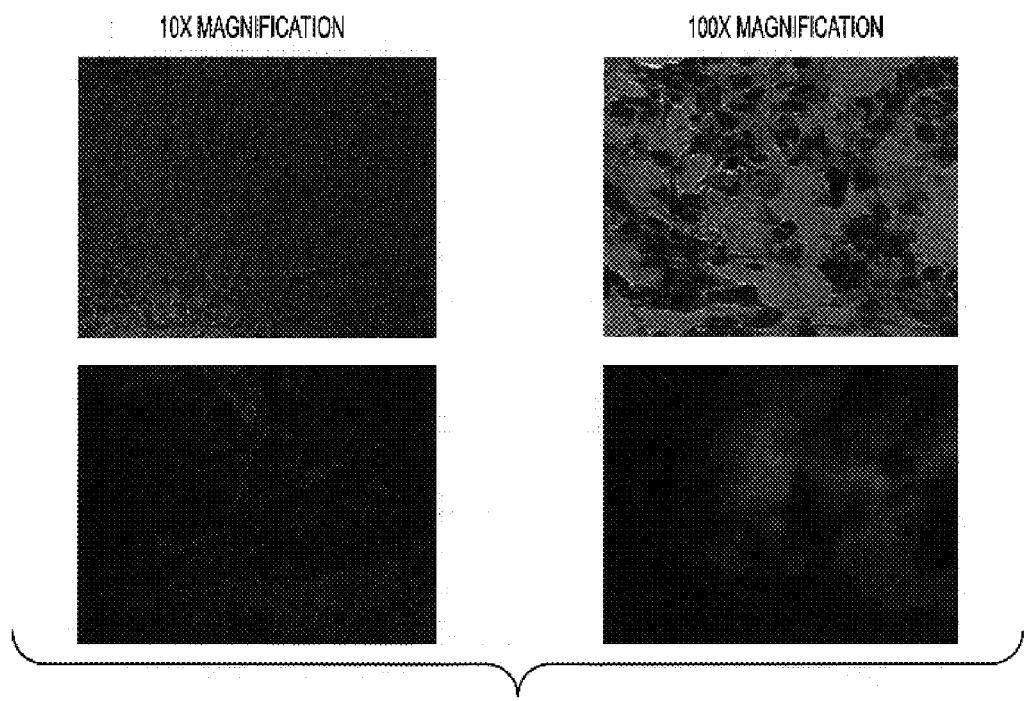
FIG. 15 shows tumor imaging in neoplastic lymph node tissue tissue.

Fluorescent cobalamin uptake. Minimum Essential Medium, alpha modification (α-MEM; 7.5% newborn calf serum, 2.5% fetal bovine serum, 0.2% nystatin, 2.5% penicillin/streptomycin, pH 7.2; Sigma) was prepared and aliquoted (10 mL) into sterile 25 mL screw top tissue culture flasks. The media was brought to 37° C., and tissue samples (neoplastic breast tissue, healthy breast tissue, neoplastic lymph node tissue and healthy lymph node tissue) were incubated with fluorescently labeled cobalamins (10 pM), cyanocoblamin (1 nM) and in α-MEM for 3 h. Human tissue samples were procured under an IRB-approved protocol. The tissue was removed from the flask, washed with Dulbecco's Phosphate Buffered Saline (DPBS; Sigma), and mounted on a brass plate at –20° C. with OCT compound (Shandon) for frozen section slicing. Tissue was sliced (4–6 µm sections) in a CTD Harris cryostat at –20° C. Thin tissue sections were pulled back with a small artist brush and fixed to a microscope slide with 100% ethanol. Slides were stained using a standard hematoxylin staining procedure: 95% ethanol, 20 seconds; water, 5 seconds; hematoxylin (Fisher), 45 seconds; water, 5 seconds; bluing solution (tap water), 10 seconds; 95% ethanol, 10 seconds; 100% ethanol, 10 seconds; xylene, 10 seconds; and xylene, 10 seconds. Slides were evaluated by phase contrast and epifluorescence microscopy at 10x, 60x, and 100x magnification. Tumor imaging in (a) neoplastic breast tissue is shown in FIG. 14 and (b) neoplastic lymph node tissue is shown in FIG. 15.

Cell viability and tissue metabolic activity assay. 3-[4,5-Dimethylthiazol-2-yl]-2,5-diphenyltetrazolium thiazolyl bromide (MTT; Sigma) was used to qualitatively determine the metabolic competency of the tissue after 3 h incubation time with fluorescent cobalamin. A portion of the tissue was removed from the media, washed with DPBS, and immersed in MTT (2 mL; 2.5 mg/mL). This tissue was incubated for 3 h under a 5% $CO_2$ atmosphere at 37° C. During this incubation period, viable cells in the tissue sample reduced the MTT dye to purple formazan by succinate dehydrogenase activity. The tissue was washed with DPBS and prepared according to the cryomicrotome procedure outlined above to ensure the metabolic competency of the tissue. It was found that in vitro both healthy and neoplastic tissue take up fluorescent cobalamins.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

Bibliography

Carmel, R. (1975). "Extreme Elevation of Serum Transcobalamin I in Patients with Metastatic Cancer." *New Engl J Med* 292:282–284.
Celis, A. and Celis, J. E. (1998). *Cell Biology*, pp. 9–11.
Collins, D. A. and Hogenkamp, H. P. C. (1997). "Transcobalamin II Receptor Imaging via Radiolabeled Diethylene-Triaminepentaacetate Cobalamin Analogs." *J Nucl Med* 38:717–723.
Collins, D. A. et al. (1999). "Tumor Imaging via Indium-111-Labeled DTPA-Adenosyl-cobalamin." *Mayo Clinic Proceedings* 74: 687–691.
Collins, D. A. et al. (2000). "Biodistribution of Radiolabeled Adenosylcobalamin in Patients Diagnosed with Various Malignancies." *Mayo Clinic Proceedings* 75:568–580.
Flodh, H. (1968). "Accumulation of labelled Vitamin B-12 in Some Transplanted Tumors." *Acta Ratiol Suppl* 284:55–60.
Hogenkamp, H. P. C., et al. (1999). "The Pharmacological Uses of Cobalamin Bioconjugates." In *The Chemistry and Biochemistry of B-12*, Banerjee, R., Ed., John Wiley & Sons, New York, pp. 385–410.
Howard, W. A. et al. (1997). "Sonolysis Promotes Indirect C—Co Bond Cleavage of Alkylcob(III)alamins." *Bioconj Chem* 8:498–502.
McGreevy, J. M. (1998). "Sentinel Lymph Node Biopsy in Breast Cancer." *Curr Surg* 55:301–4.
Mitchell, A. M. et al. (1999). "Targeting Leukemia Cells with Cobalamin Bioconjugates" In *Enzymatic Mechanisms*, Frey, P. A.; Northrop, D. B., Eds., pp 150–154.
McMasters, K. M. et al. (1999). "Sentinel Lymph Node Biopsy for Breast Cancer—Not yet the Standard of Care." *New England J Med* 339:990.
Morton, D. L. et al. (1992). "Technical Details of Intraoperative Lymphatic Mapping for Early Stage Melanoma." *Arch Surg* 127:392–9.
Rachmilewitz, B, et al. (1971). , "Serum Transcobalamin in Myeloid Leukemia." *J Lab Clin Med* 78:275.
Schneider, Z. and Stroinski, A. (1987). *Comprehensive $B_{12}$*, de Gruyter, Berlin, pp. 358.

What is claimed is:

1. A cobalamin having the general formula

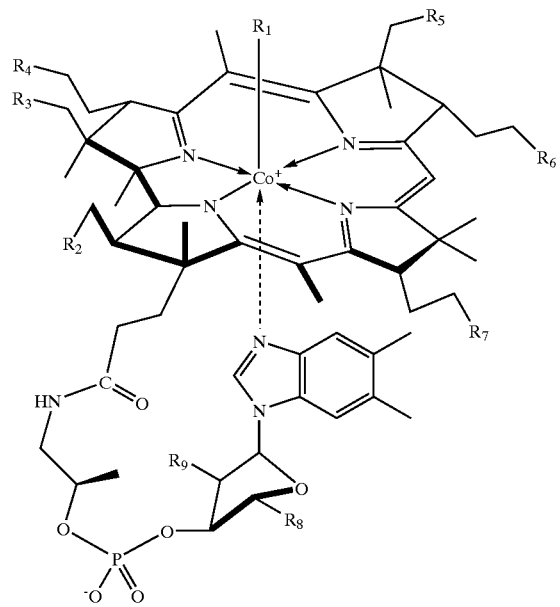

where $R_1$ is CN, OH, $OH_2$, $CH_3$, 5'-(5'-deoxyadenosyl) or $(CH_2)_p NHC(=S)Y$; $R_2$, $R_3$, $R_4$, $R_5$, $R_6$, and $R_7$ are $CONH_2$; $R_8$ is $CH_2OH$ or $CH_2O(C=O)X_m Y$; $R_9$ is OH or $O(C=O)X_m Y$; X is a linker having the formula $NH(CH_2)_n NHO(C=O)$ or $NH-(CH_2)_n-NH$; Y is a fluorophore, a phosphorophore, or a chemiluminescent chromophore; m is 0 or 1, n is 0–50 and p is 2–10, with the proviso that at least one of $R_1$, $R_8$ and $R_9$ groups has Y, wherein said cobalamin fluoresces, phosphoresces or luminesces when illuminated with ultraviolet, visible, or infrared light without cleavage of Y from the cobalamin.

2. The cobalamin of claim 1, wherein $R_8$ contains the fluorophore, phosphorophore, or chemiluminescent chromophore.

3. The cobalamin of claim 1, wherein $R_1$ contains the fluorophore, phosphorophore, or chemiluminescent chromophore.

4. The cobalamin of claim 1, wherein $R_9$ contains the fluorophore, phosphorophore, or chemiluminescent chromophore.

5. A method for the identification of cancer tissue or tissue containing cancerous cells of an individual which comprises contacting the cobalamin of claim 1 with tissue suspected of being cancerous or containing cancerous cells, illuminating said tissue with ultraviolet, visible or infrared light, and detecting differences in the emitted fluorescence, phosphorescence or luminescence compared to non-cancerous tissue or cells.

6. The method of claim 5, wherein said tissue suspected of containing cancerous cells is a lymph node.

7. The method of claim 6, wherein said lymph node is a sentinel lymph node or an axillary lymph node.

8. The method of claim 5, where the fluorescent cobalamin is injected into a lymph duct.

9. The method of claim 5, wherein the identification is performed microscopically, visually or transdermally.

10. The method of claim 5, wherein said sample is obtained from said individual by biopsy.

11. A method for visually differentiating cancerous tissue from healthy tissue of an individual which comprises contacting the cobalamin of claim 1 with tissue from said individual, illuminating said tissue and visually detecting fluorescence, phosphorescence or luminescence, whereby said cancerous tissue fluoresces, phosphoresces or luminesces and said healthy tissue exhibits less fluorescence, phosphorescence or luminescence.

12. A method for defining tumor margins in vivo, ex vivo, or in situ which comprises contacting the cobalamin of claim 1 with tissue from said individual suspected of containing a tumor, illuminating said tissue and detecting fluorescence, phosphorescence or luminescence, whereby said tumor tissue fluoresces, phosphoresces or luminesces and defines the margin of the tumor.

13. A method for identifying metastatic cancer in an individual which comprises contacting the cobalamin of claim 1 with tissue or cells suspected of being metastatic cancer from said individual, illuminating said tissue and detecting fluorescence, phosphorescence or luminescence, whereby said metastatic cancer tissue or cells fluoresce, phosphoresce or luminesce.

14. The method of claim 13, wherein the identification is performed visually, transdermally or microscopically.

15. A method to diagnose, detect, or monitor cancer in vivo, ex vivo, or in situ which comprises contacting the cobalamin of claim 1 with tissue or cells from said individual, illuminating said tissue and detecting fluorescence, phosphorescence or luminescence, whereby cancer tissue or cells fluoresce, phosphoresce or luminesce and healthy tissue exhibits less fluorescence, phosphorescence or luminescence.

16. The method of claim 15, wherein the contacting is performed by administering the cobalamin to said individual intravenously, intrathecally, intramuscularly, intratumorally, intralymphatically or orally.

17. The method of claim 16, wherein the contacting is performed intraoperatively.

18. The method of claim 17, wherein the contacting is performed in the course of a clinical pathology evaluation of tissue and cells.

19. A method to identify metastatic disease in the treatment, diagnosis, detection, or monitoring of cancer in an individual which comprises contacting the cobalamin of claim 1 with tissue or cells from said individual, illuminating said tissue and detecting fluorescence, whereby cancer tissue or cells fluoresce, phosphoresce or luminesce and healthy tissue exhibits less fluorescence, phosphorescence or luminescence.

20. The method of claim 19, wherein said cancer is breast cancer, colon cancer, ovarian cancer, lung cancer, prostate cancer, liver cancer or melanoma.

21. The method of claim 19, wherein said cancer is carcinoma that has spread via the lymphatic system.

22. The method of claim 19, wherein said cancer is lymphoma or leukemia.

23. The method of claim 22, wherein said tissue is bone marrow aspirate or peripheral blood.

24. The method of claim 19, which utilizes flow cytometry or automatic analysis of body fluids.

25. A method to determine the stage of cancer progression which comprises contacting the cobalamin of claim 1 with cancer cells, illuminating said cancer cells, and detecting fluorescence, phosphorescence or luminescence whereby the response of cancer cells to cobalamin-based therapy is directly proportional to the fluorescence, phosphorescence or luminescence of said cancer cells compared to noncancerous cells.

26. A method to assay an amount of cobalamin in a sample which comprises performing a competitive binding assay on said sample by administration of a cobalamin of claim 1 and determining the amount of cobalamin present in said sample.

27. A method to assay an amount of nonsaturated cobalamin binding capacity of cobalamin binding proteins in a sample which comprises performing a competitive binding assay on cobalamin binding proteins isolated from said sample by administration of a cobalamin of claim 1 and determining the amount of nonsaturated cobalamin binding capacity in said sample.

28. A method to assay an amount of cobalamin bound to cobalamin binding proteins in a sample which comprises performing a competitive binding assay of cobalamin separated from cobalamin binding proteins isolated from said sample by administration of a cobalamin of claim 1 and determining the amount of cobalamin bound to said proteins in said sample.

* * * * *